(12) United States Patent
Sorensen

(10) Patent No.: US 7,097,971 B2
(45) Date of Patent: Aug. 29, 2006

(54) HIV-1 PEPTIDE, ANTIGEN, IMMUNOGENIC COMPOSITION, DIAGNOSTIC METHOD AND IMMUNOASSAY KIT

(75) Inventor: Birger Sorensen, Skien (NO)

(73) Assignee: Bionor Immuno AS, Skien (NO)

( * ) Notice: Subject to any disclaimer, the term of this patent is extended or adjusted under 35 U.S.C. 154(b) by 510 days.

(21) Appl. No.: 10/129,333

(22) PCT Filed: Sep. 3, 2001

(86) PCT No.: PCT/NO01/00363

§ 371 (c)(1),
(2), (4) Date: Jun. 11, 2002

(87) PCT Pub. No.: WO02/20555

PCT Pub. Date: Mar. 14, 2002

(65) Prior Publication Data

US 2005/0053616 A1    Mar. 10, 2005

(30) Foreign Application Priority Data

Sep. 4, 2000   (NO) ................................. 20004412

(51) Int. Cl.
*C12Q 1/70* (2006.01)
(52) U.S. Cl. ........................... 435/5; 435/7.1; 435/974; 435/975; 530/324; 530/325; 530/326; 530/329; 530/826; 424/188.1; 424/193.1; 424/196.11; 424/208.1
(58) Field of Classification Search ................ 530/324, 530/325, 326, 329, 826; 424/188.1, 193.1, 424/196.11, 208.1; 435/5, 7.1, 974, 975
See application file for complete search history.

(56) References Cited

U.S. PATENT DOCUMENTS

| 5,595,884 | A  | * | 1/1997  | Androphy et al. ........ 435/69.1 |
| 6,706,859 | B1 |   | 3/2004  | Sörensen |
| 2004/0259797 | A1 |   | 12/2004 | Sorensen |

FOREIGN PATENT DOCUMENTS

| FR | 2773156 | 7/1999 |
| WO | 94/15634 | 7/1994 |
| WO | 9415634 | 7/1994 |
| WO | 9627389 | 9/1996 |
| WO | 99/02185 | 1/1999 |
| WO | 9902185 | 1/1999 |
| WO | 99/27958 | 6/1999 |
| WO | 9927958 | 6/1999 |
| WO | 0078969 | 12/2000 |

OTHER PUBLICATIONS

Goldstein, "HIV-1 Tat protein as a potential AIDS vaccine", Nature Medicine, vol. 2, No. 9 (Sep. 1996), pp. 960-964.*
Riffkin et al. "A single amino-acid change between the antigenically different extracellular serine proteases V2 and B2 from *Dichelobacter nodosus*", Gene, vol. 167 (1995), pp. 279-283.*
Abaza et al. "Effect of amino acid substitutions outside an antigenic site on protein binding to monoclonal antibodies of predetermined specificity obtained by peptide immunization", Journal of Protein Chemistry, vol. 11, No. 5 (1992), pp. 433-444.*
Cruse et al. Illustrated Dictionary of Immunology (Boca Raton, FL, CRC Press, Inc., 1995), p. 309. QR180.4.C78.*
Paul, Fundamental Immunology, (Philadelphia & New York, Lippincott-Raven Publishers, 1993), pp. 250 and 1311-1312. QR181.F84.*
Cohen et al. "Pronounced acute immunosuppression in vivo mediated by HIV Tat challenge", Proceedings of the National Academy of Sciences of the United States of America, vol. 96, Issue 19(Sep. 14, 1999), pp. 10842 10847.*
Blazevic et al., Aids Research and Human Retroviruses, vol. 11, No. 11, 1995, pp. 1335-1342.
G. Goldstein, "HIV-1 Tat protein as a potential AIDS vaccine", Nature Medicine, vol. 2, No. 9, Sep. 1996, pp. 960-964.

* cited by examiner

*Primary Examiner*—Jeffrey Stucker
(74) *Attorney, Agent, or Firm*—Wenderoth, Lind & Ponack, L.L.P.

(57) ABSTRACT

The present invention comprises novel and modified peptides capable of inducing a HIV-1 specific immune response without antagonizing the cytotoxic T-cell activity in order to achieve an effective prophylactic and therapeutic vaccine against HIV. The peptides are based on conserved regions of HIV Tat and Rev, regulatory proteins and Nef, auxiliary proteins. Antigens in free- or carrier-bound form comprising at least one of the said peptides, vaccine compositions containing at least one of the antigens, immunoassay kits and a method of detecting antibodies induced by HIV or HIV specific peptides using such antigens, are described.

9 Claims, No Drawings

SEQUENCE LISTING

```
<160> NUMBER OF SEQ ID NOS: 18

<210> SEQ ID NO 1
<211> LENGTH: 24
<212> TYPE: PRT
<213> ORGANISM: Artificial Sequence
<220> FEATURE:
<221> NAME/KEY: variant
<222> LOCATION: (1)
<223> OTHER INFORMATION: Met, Ser, Cys or None
<220> FEATURE:
<221> NAME/KEY: variant
<222> LOCATION: (2)
<223> OTHER INFORMATION: Glu, Asp, Val, Ser or None
<220> FEATURE:
<221> NAME/KEY: variant
<222> LOCATION: (3)
<223> OTHER INFORMATION: Ser, Gln, Pro, Leu, Val, Ala, Trp, Tyr or Phe
<220> FEATURE:
<221> NAME/KEY: variant
<222> LOCATION: (4)
<223> OTHER INFORMATION: Val or Ile
<220> FEATURE:
<221> NAME/KEY: variant
<222> LOCATION: (5)
<223> OTHER INFORMATION: Asp, Asn or Ile
```

-continued

```
<220> FEATURE:
<221> NAME/KEY: variant
<222> LOCATION: (6)
<223> OTHER INFORMATION: Pro, His or Ala
<220> FEATURE:
<221> NAME/KEY: variant
<222> LOCATION: (7)
<223> OTHER INFORMATION: Arg, Asn, Ser, Lys, Glu or Asp
<220> FEATURE:
<221> NAME/KEY: variant
<222> LOCATION: (8)
<223> OTHER INFORMATION: Leu
<220> FEATURE:
<221> NAME/KEY: variant
<222> LOCATION: (9)
<223> OTHER INFORMATION: Glu
<220> FEATURE:
<221> NAME/KEY: variant
<222> LOCATION: (10)
<223> OTHER INFORMATION: Pro
<220> FEATURE:
<221> NAME/KEY: variant
<222> LOCATION: (11)
<223> OTHER INFORMATION: Trp
<220> FEATURE:
<221> NAME/KEY: variant
<222> LOCATION: (12)
<223> OTHER INFORMATION: Leu, Ile or Nle
<220> FEATURE:
<221> NAME/KEY: variant
<222> LOCATION: (13)
<223> OTHER INFORMATION: His
<220> FEATURE:
<221> NAME/KEY: variant
<222> LOCATION: (14)
<223> OTHER INFORMATION: Pro
<220> FEATURE:
<221> NAME/KEY: variant
<222> LOCATION: (15)
<223> OTHER INFORMATION: Gly or Pro
<220> FEATURE:
<221> NAME/KEY: variant
<222> LOCATION: (16)
<223> OTHER INFORMATION: Ser, Asn or Ala
<220> FEATURE:
<221> NAME/KEY: variant
<222> LOCATION: (17)
<223> OTHER INFORMATION: Gln, Lys or Thr
<220> FEATURE:
<221> NAME/KEY: variant
<222> LOCATION: (18)
<223> OTHER INFORMATION: Pro or His
<220> FEATURE:
<221> NAME/KEY: variant
<222> LOCATION: (19)
<223> OTHER INFORMATION: Lys, Thr, Ser, Ala, Arg, Pro, Glu, Leu, Ile or
      Nle
<220> FEATURE:
<221> NAME/KEY: variant
<222> LOCATION: (20)
<223> OTHER INFORMATION: Thr, Ala or Ile
<220> FEATURE:
<221> NAME/KEY: variant
<222> LOCATION: (21)
<223> OTHER INFORMATION: Ala, Pro, Asp, or Val
<220> FEATURE:
<221> NAME/KEY: variant
<222> LOCATION: (22)
<223> OTHER INFORMATION: Cys or Ser
<220> FEATURE:
<221> NAME/KEY: variant
<222> LOCATION: (23)
<223> OTHER INFORMATION: Thr, Asn or Ser
<220> FEATURE:
<221> NAME/KEY: variant
<222> LOCATION: (24)
<223> OTHER INFORMATION: Asn, Lys, Arg, Gln, Ala, Pro or Thr
<220> FEATURE:
<223> OTHER INFORMATION: Description of Artificial Sequence: SYNTHETIC
```

```
                     CONSTRUCT

<400> SEQUENCE: 1

Xaa Xaa Xaa Xaa Xaa Xaa Xaa Leu Glu Pro Trp Xaa His Pro Xaa Xaa
 1               5                  10                  15

Xaa Xaa Xaa Xaa Xaa Xaa Xaa Xaa
            20

<210> SEQ ID NO 2
<211> LENGTH: 24
<212> TYPE: PRT
<213> ORGANISM: Artificial Sequence
<220> FEATURE:
<221> NAME/KEY: variant
<222> LOCATION: (1)
<223> OTHER INFORMATION: Cys
<220> FEATURE:
<221> NAME/KEY: variant
<222> LOCATION: (2)
<223> OTHER INFORMATION: Ser
<220> FEATURE:
<221> NAME/KEY: variant
<222> LOCATION: (3)
<223> OTHER INFORMATION: Trp
<220> FEATURE:
<221> NAME/KEY: variant
<222> LOCATION: (4)
<223> OTHER INFORMATION: Val
<220> FEATURE:
<221> NAME/KEY: variant
<222> LOCATION: (5)
<223> OTHER INFORMATION: Asn
<220> FEATURE:
<221> NAME/KEY: variant
<222> LOCATION: (6)
<223> OTHER INFORMATION: Pro
<220> FEATURE:
<221> NAME/KEY: variant
<222> LOCATION: (7)
<223> OTHER INFORMATION: Arg
<220> FEATURE:
<221> NAME/KEY: variant
<222> LOCATION: (8)
<223> OTHER INFORMATION: Leu
<220> FEATURE:
<221> NAME/KEY: variant
<222> LOCATION: (9)
<223> OTHER INFORMATION: Glu
<220> FEATURE:
<221> NAME/KEY: variant
<222> LOCATION: (10)
<223> OTHER INFORMATION: Pro
<220> FEATURE:
<221> NAME/KEY: variant
<222> LOCATION: (11)
<223> OTHER INFORMATION: Trp
<220> FEATURE:
<221> NAME/KEY: variant
<222> LOCATION: (12)
<223> OTHER INFORMATION: Nle
<220> FEATURE:
<221> NAME/KEY: variant
<222> LOCATION: (13)
<223> OTHER INFORMATION: His
<220> FEATURE:
<221> NAME/KEY: variant
<222> LOCATION: (14)
<223> OTHER INFORMATION: Pro
<220> FEATURE:
<221> NAME/KEY: variant
<222> LOCATION: (15)
<223> OTHER INFORMATION: Gly
<220> FEATURE:
<221> NAME/KEY: variant
<222> LOCATION: (16)
<223> OTHER INFORMATION: Ser
```

```
<220> FEATURE:
<221> NAME/KEY: variant
<222> LOCATION: (17)
<223> OTHER INFORMATION: Gln
<220> FEATURE:
<221> NAME/KEY: variant
<222> LOCATION: (18)
<223> OTHER INFORMATION: His
<220> FEATURE:
<221> NAME/KEY: variant
<222> LOCATION: (19)
<223> OTHER INFORMATION: Nle
<220> FEATURE:
<221> NAME/KEY: variant
<222> LOCATION: (20)
<223> OTHER INFORMATION: Thr
<220> FEATURE:
<221> NAME/KEY: variant
<222> LOCATION: (21)
<223> OTHER INFORMATION: Ala
<220> FEATURE:
<221> NAME/KEY: variant
<222> LOCATION: (22)
<223> OTHER INFORMATION: Cys
<220> FEATURE:
<221> NAME/KEY: variant
<222> LOCATION: (23)
<223> OTHER INFORMATION: Thr
<220> FEATURE:
<221> NAME/KEY: variant
<222> LOCATION: (24)
<223> OTHER INFORMATION: Asn
<220> FEATURE:
<223> OTHER INFORMATION: Description of Artificial Sequence: SYNTHETIC
      CONSTRUCT

<400> SEQUENCE: 2

Cys Ser Trp Val Asn Pro Arg Leu Glu Pro Trp Xaa His Pro Gly Ser Gln His
  1               5                  10                  15

Xaa Thr Ala Cys Thr Asn
        20

<210> SEQ ID NO 3
<211> LENGTH: 22
<212> TYPE: PRT
<213> ORGANISM: Artificial Sequence
<220> FEATURE:
<221> NAME/KEY: variant
<222> LOCATION: (1)
<223> OTHER INFORMATION: Phe
<220> FEATURE:
<221> NAME/KEY: variant
<222> LOCATION: (2)
<223> OTHER INFORMATION: Val
<220> FEATURE:
<221> NAME/KEY: variant
<222> LOCATION: (3)
<223> OTHER INFORMATION: Ile
<220> FEATURE:
<221> NAME/KEY: variant
<222> LOCATION: (4)
<223> OTHER INFORMATION: Pro
<220> FEATURE:
<221> NAME/KEY: variant
<222> LOCATION: (5)
<223> OTHER INFORMATION: Arg
<220> FEATURE:
<221> NAME/KEY: variant
<222> LOCATION: (6)
<223> OTHER INFORMATION: Leu
<220> FEATURE:
<221> NAME/KEY: variant
<222> LOCATION: (7)
<223> OTHER INFORMATION: Glu
<220> FEATURE:
<221> NAME/KEY: variant
```

```
<222> LOCATION: (8)
<223> OTHER INFORMATION: Pro
<220> FEATURE:
<221> NAME/KEY: variant
<222> LOCATION: (9)
<223> OTHER INFORMATION: Trp
<220> FEATURE:
<221> NAME/KEY: variant
<222> LOCATION: (10)
<223> OTHER INFORMATION: Nle
<220> FEATURE:
<221> NAME/KEY: variant
<222> LOCATION: (11)
<223> OTHER INFORMATION: His
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Ser
<220> FEATURE:
<221> NAME/KEY: variant
<222> LOCATION: (15)
<223> OTHER INFORMATION: Gln
<220> FEATURE:
<221> NAME/KEY: variant
<222> LOCATION: (16)
<223> OTHER INFORMATION: Pro
<220> FEATURE:
<221> NAME/KEY: variant
<222> LOCATION: (17)
<223> OTHER INFORMATION: Nle
<220> FEATURE:
<221> NAME/KEY: variant
<222> LOCATION: (18)
<223> OTHER INFORMATION: Thr
<220> FEATURE:
<221> NAME/KEY: variant
<222> LOCATION: (19)
<223> OTHER INFORMATION: Ala
<220> FEATURE:
<221> NAME/KEY: variant
<222> LOCATION: (20)
<223> OTHER INFORMATION: Cys
<220> FEATURE:
<221> NAME/KEY: variant
<222> LOCATION: (21)
<223> OTHER INFORMATION: Thr
<220> FEATURE:
<221> NAME/KEY: variant
<222> LOCATION: (22)
<223> OTHER INFORMATION: Asn
<220> FEATURE:
<223> OTHER INFORMATION: Description of Artificial Sequence: SYNTHETIC
      CONSTRUCT

<400> SEQUENCE: 3

Phe Val Ile Pro Arg Leu Glu Pro Trp Xaa His Pro Gly Ser Gln Pro Xaa Thr
  1               5                  10                  15

Ala Cys Thr Asn
     20

<210> SEQ ID NO 4
<211> LENGTH: 27
<212> TYPE: PRT
<213> ORGANISM: Artificial Sequence
<220> FEATURE:
<221> NAME/KEY: variant
<222> LOCATION: (1)
<223> OTHER INFORMATION: Pro, Ile, Leu, Thr, Tyr or Val
```

```
<220> FEATURE:
<221> NAME/KEY: variant
<222> LOCATION: (2)
<223> OTHER INFORMATION: Val, Ala, Cys or Leu
<220> FEATURE:
<221> NAME/KEY: variant
<222> LOCATION: (3)
<223> OTHER INFORMATION: Cys, Ile, Leu, Val or Nle
<220> FEATURE:
<221> NAME/KEY: Variant
<222> LOCATION: (4)
<223> OTHER INFORMATION: Phe
<220> FEATURE:
<221> NAME/KEY: variant
<222> LOCATION: (5)
<223> OTHER INFORMATION: Ile, Leu, Gln, Met or Thr
<220> FEATURE:
<221> NAME/KEY: variant
<222> LOCATION: (6)
<223> OTHER INFORMATION: Thr, Asn, Lys or Arg
<220> FEATURE:
<221> NAME/KEY: variant
<222> LOCATION: (7)
<223> OTHER INFORMATION: Lys, Arg or Gln
<220> FEATURE:
<221> NAME/KEY: variant
<222> LOCATION: (8)
<223> OTHER INFORMATION: Gly or Ala
<220> FEATURE:
<221> NAME/KEY: variant
<222> LOCATION: (9)
<223> OTHER INFORMATION: Leu or Ile
<220> FEATURE:
<221> NAME/KEY: variant
<222> LOCATION: (10)
<223> OTHER INFORMATION: Gly, Ser or Ala
<220> FEATURE:
<221> NAME/KEY: variant
<222> LOCATION: (11)
<223> OTHER INFORMATION: Ile or Gly
<220> FEATURE:
<221> NAME/KEY: variant
<222> LOCATION: (12)
<223> OTHER INFORMATION: Ser, Phe or Tyr
<220> FEATURE:
<221> NAME/KEY: variant
<222> LOCATION: (13)
<223> OTHER INFORMATION: Gly or None or PEG linker
<220> FEATURE:
<221> NAME/KEY: variant
<222> LOCATION: (14)
<223> OTHER INFORMATION: Gly or None or PEG linker
<220> FEATURE:
<221> NAME/KEY: variant
<222> LOCATION: (15)
<223> OTHER INFORMATION: Gly or None or PEG linker
<220> FEATURE:
<221> NAME/KEY: variant
<222> LOCATION: (16)
<223> OTHER INFORMATION: Tyr
<220> FEATURE:
<221> NAME/KEY: variant
<222> LOCATION: (17)
<223> OTHER INFORMATION: Leu, Ile or Nle
<220> FEATURE:
<221> NAME/KEY: variant
<222> LOCATION: (18)
<223> OTHER INFORMATION: Gly
<220> FEATURE:
<221> NAME/KEY: variant
<222> LOCATION: (19)
<223> OTHER INFORMATION: Arg, Lys, Ser or Cit
<220> FEATURE:
<221> NAME/KEY: variant
<222> LOCATION: (20)
<223> OTHER INFORMATION: Lys
<220> FEATURE:
<221> NAME/KEY: variant
<222> LOCATION: (21)
```

```
<223> OTHER INFORMATION: Lys
<220> FEATURE:
<221> NAME/KEY: variant
<222> LOCATION: (22)
<223> OTHER INFORMATION: Arg
<220> FEATURE:
<221> NAME/KEY: variant
<222> LOCATION: (23)
<223> OTHER INFORMATION: Arg, Lys, Ser, Gly or Cit
<220> FEATURE:
<221> NAME/KEY: variant
<222> LOCATION: (24)
<223> OTHER INFORMATION: Gly, Arg or Pro
<220> FEATURE:
<221> NAME/KEY: variant
<222> LOCATION: (25)
<223> OTHER INFORMATION: Ile or Leu
<220> FEATURE:
<221> NAME/KEY: variant
<222> LOCATION: (26)
<223> OTHER INFORMATION: Gly, Leu, Ile, Cys or None
<220> FEATURE:
<221> NAME/KEY: variant
<222> LOCATION: (27)
<223> OTHER INFORMATION: Gly or None
<220> FEATURE:
<223> OTHER INFORMATION: Description of Artificial Sequence: SYNTHETIC
      CONSTRUCT

<400> SEQUENCE: 4

Xaa Xaa Xaa Phe Xaa Xaa Xaa Xaa Xaa Xaa Xaa Xaa Xaa Xaa Xaa Tyr Xaa Gly
  1               5                  10                  15

Xaa Lys Lys Arg Xaa Xaa Xaa Xaa Xaa
        20                  25

<210> SEQ ID NO 5
<211> LENGTH: 27
<212> TYPE: PRT
<213> ORGANISM: Artificial Sequence
<220> FEATURE:
<221> NAME/KEY: variant
<222> LOCATION: (1)
<223> OTHER INFORMATION: Tyr
<220> FEATURE:
<221> NAME/KEY: variant
<222> LOCATION: (2)
<223> OTHER INFORMATION: Leu
<220> FEATURE:
<221> NAME/KEY: variant
<222> LOCATION: (3)
<223> OTHER INFORMATION: Leu
<220> FEATURE:
<221> NAME/KEY: Variant
<222> LOCATION: (4)
<223> OTHER INFORMATION: Phe
<220> FEATURE:
<221> NAME/KEY: variant
<222> LOCATION: (5)
<223> OTHER INFORMATION: Leu
<220> FEATURE:
<221> NAME/KEY: variant
<222> LOCATION: (6)
<223> OTHER INFORMATION: Thr
<220> FEATURE:
<221> NAME/KEY: variant
<222> LOCATION: (7)
<223> OTHER INFORMATION: Lys
<220> FEATURE:
<221> NAME/KEY: variant
<222> LOCATION: (8)
<223> OTHER INFORMATION: Gly
<220> FEATURE:
<221> NAME/KEY: variant
<222> LOCATION: (9)
<223> OTHER INFORMATION: Leu
<220> FEATURE:
```

```
<221> NAME/KEY: variant
<222> LOCATION: (10)
<223> OTHER INFORMATION: Gly
<220> FEATURE:
<221> NAME/KEY: variant
<222> LOCATION: (11)
<223> OTHER INFORMATION: Ile
<220> FEATURE:
<221> NAME/KEY: variant
<222> LOCATION: (12)
<223> OTHER INFORMATION: Ser
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Gly
<220> FEATURE:
<221> NAME/KEY: variant
<222> LOCATION: (15)
<223> OTHER INFORMATION: Gly
<220> FEATURE:
<221> NAME/KEY: variant
<222> LOCATION: (16)
<223> OTHER INFORMATION: Tyr
<220> FEATURE:
<221> NAME/KEY: variant
<222> LOCATION: (17)
<223> OTHER INFORMATION: Nle
<220> FEATURE:
<221> NAME/KEY: variant
<222> LOCATION: (18)
<223> OTHER INFORMATION: Gly
<220> FEATURE:
<221> NAME/KEY: variant
<222> LOCATION: (19)
<223> OTHER INFORMATION: Cit
<220> FEATURE:
<221> NAME/KEY: variant
<222> LOCATION: (20)
<223> OTHER INFORMATION: Lys
<220> FEATURE:
<221> NAME/KEY: variant
<222> LOCATION: (21)
<223> OTHER INFORMATION: Lys
<220> FEATURE:
<221> NAME/KEY: variant
<222> LOCATION: (22)
<223> OTHER INFORMATION: Arg
<220> FEATURE:
<221> NAME/KEY: variant
<222> LOCATION: (23)
<223> OTHER INFORMATION: Cit
<220> FEATURE:
<221> NAME/KEY: variant
<222> LOCATION: (24)
<223> OTHER INFORMATION: Gln
<220> FEATURE:
<221> NAME/KEY: variant
<222> LOCATION: (25)
<223> OTHER INFORMATION: Ile
<220> FEATURE:
<221> NAME/KEY: variant
<222> LOCATION: (26)
<223> OTHER INFORMATION: Leu
<220> FEATURE:
<221> NAME/KEY: variant
<222> LOCATION: (27)
<223> OTHER INFORMATION: Gly
<220> FEATURE:
<223> OTHER INFORMATION: Description of Artificial Sequence: SYNTHETIC
      CONSTRUCT

<400> SEQUENCE: 5

Tyr Leu Leu Phe Leu Thr Lys Gly Leu Gly Ile Ser Gly Gly Gly Tyr Xaa Gly
 1               5                  10                  15
```

```
Xaa Lys Lys Arg Xaa Gln Ile Leu Gly
    20                  25
```

```
<210> SEQ ID NO 6
<211> LENGTH: 27
<212> TYPE: PRT
<213> ORGANISM: Artificial Sequence
<220> FEATURE:
<221> NAME/KEY: variant
<222> LOCATION: (1)
<223> OTHER INFORMATION: Tyr
<220> FEATURE:
<221> NAME/KEY: variant
<222> LOCATION: (2)
<223> OTHER INFORMATION: Leu
<220> FEATURE:
<221> NAME/KEY: variant
<222> LOCATION: (3)
<223> OTHER INFORMATION: Nle
<220> FEATURE:
<221> NAME/KEY: Variant
<222> LOCATION: (4)
<223> OTHER INFORMATION: Phe
<220> FEATURE:
<221> NAME/KEY: variant
<222> LOCATION: (5)
<223> OTHER INFORMATION: Leu
<220> FEATURE:
<221> NAME/KEY: variant
<222> LOCATION: (6)
<223> OTHER INFORMATION: Thr
<220> FEATURE:
<221> NAME/KEY: variant
<222> LOCATION: (7)
<223> OTHER INFORMATION: Arg
<220> FEATURE:
<221> NAME/KEY: variant
<222> LOCATION: (8)
<223> OTHER INFORMATION: Gly
<220> FEATURE:
<221> NAME/KEY: variant
<222> LOCATION: (9)
<223> OTHER INFORMATION: Leu
<220> FEATURE:
<221> NAME/KEY: variant
<222> LOCATION: (10)
<223> OTHER INFORMATION: Gly
<220> FEATURE:
<221> NAME/KEY: variant
<222> LOCATION: (11)
<223> OTHER INFORMATION: Ile
<220> FEATURE:
<221> NAME/KEY: variant
<222> LOCATION: (12)
<223> OTHER INFORMATION: Ser
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Gly
<220> FEATURE:
<221> NAME/KEY: variant
<222> LOCATION: (15)
<223> OTHER INFORMATION: Gly
<220> FEATURE:
<221> NAME/KEY: variant
<222> LOCATION: (16)
<223> OTHER INFORMATION: Tyr
<220> FEATURE:
<221> NAME/KEY: variant
<222> LOCATION: (17)
<223> OTHER INFORMATION: Nle
<220> FEATURE:
<221> NAME/KEY: variant
```

```
<222> LOCATION: (18)
<223> OTHER INFORMATION: Gly
<220> FEATURE:
<221> NAME/KEY: variant
<222> LOCATION: (19)
<223> OTHER INFORMATION: Cit
<220> FEATURE:
<221> NAME/KEY: variant
<222> LOCATION: (20)
<223> OTHER INFORMATION: Lys
<220> FEATURE:
<221> NAME/KEY: variant
<222> LOCATION: (21)
<223> OTHER INFORMATION: Lys
<220> FEATURE:
<221> NAME/KEY: variant
<222> LOCATION: (22)
<223> OTHER INFORMATION: Arg
<220> FEATURE:
<221> NAME/KEY: variant
<222> LOCATION: (23)
<223> OTHER INFORMATION: Cit
<220> FEATURE:
<221> NAME/KEY: variant
<222> LOCATION: (24)
<223> OTHER INFORMATION: Gln
<220> FEATURE:
<221> NAME/KEY: variant
<222> LOCATION: (25)
<223> OTHER INFORMATION: Ile
<220> FEATURE:
<221> NAME/KEY: variant
<222> LOCATION: (26)
<223> OTHER INFORMATION: Cys
<220> FEATURE:
<221> NAME/KEY: variant
<222> LOCATION: (27)
<223> OTHER INFORMATION: Gly
<220> FEATURE:
<223> OTHER INFORMATION: Description of Artificial Sequence: SYNTHETIC
      CONSTRUCT

<400> SEQUENCE: 6

Tyr Leu Xaa Phe Leu Thr Arg Gly Leu Gly Ile Ser Gly Gly Gly Tyr Xaa Gly
  1               5                  10                  15

Xaa Lys Lys Arg Xaa Gln Ile Cys Gly
     20                  25

<210> SEQ ID NO 7
<211> LENGTH: 28
<212> TYPE: PRT
<213> ORGANISM: Artificial Sequence
<220> FEATURE:
<221> NAME/KEY: variant
<222> LOCATION: (1)
<223> OTHER INFORMATION: Phe, Tyr, Trp or Arg
<220> FEATURE:
<221> NAME/KEY: variant
<222> LOCATION: (2)
<223> OTHER INFORMATION: Ile
<220> FEATURE:
<221> NAME/KEY: variant
<222> LOCATION: (3)
<223> OTHER INFORMATION: Leu
<220> FEATURE:
<221> NAME/KEY: variant
<222> LOCATION: (4)
<223> OTHER INFORMATION: Gly, Ser, Asn, Asp, Cys, Val, Thr, Ala or Arg
<220> FEATURE:
<221> NAME/KEY: variant
<222> LOCATION: (5)
<223> OTHER INFORMATION: Thr, Ala, Asp, Asn or Ser
<220> FEATURE:
<221> NAME/KEY: variant
<222> LOCATION: (6)
<223> OTHER INFORMATION: Tyr, Cys, Phe, Arg, His, Ser, Val or Leu
```

```
-continued

<220> FEATURE:
<221> NAME/KEY: variant
<222> LOCATION: (7)
<223> OTHER INFORMATION: Leu
<220> FEATURE:
<221> NAME/KEY: variant
<222> LOCATION: (8)
<223> OTHER INFORMATION: Gly
<220> FEATURE:
<221> NAME/KEY: variant
<222> LOCATION: (9)
<223> OTHER INFORMATION: Arg
<220> FEATURE:
<221> NAME/KEY: variant
<222> LOCATION: (10)
<223> OTHER INFORMATION: Ser, Pro, Phe, Leu or Ile
<220> FEATURE:
<221> NAME/KEY: variant
<222> LOCATION: (11)
<223> OTHER INFORMATION: Ala, Thr, Glu, Gln, Val, Pro or Ser
<220> FEATURE:
<221> NAME/KEY: variant
<222> LOCATION: (12)
<223> OTHER INFORMATION: Gly or None or PEG linker
<220> FEATURE:
<221> NAME/KEY: variant
<222> LOCATION: (13)
<223> OTHER INFORMATION: Gly or None or PEG linker
<220> FEATURE:
<221> NAME/KEY: variant
<222> LOCATION: (14)
<223> OTHER INFORMATION: Gly or None or PEG linker
<220> FEATURE:
<221> NAME/KEY: variant
<222> LOCATION: (15)
<223> OTHER INFORMATION: Glu, Lys, Gln, Asp, Asn, Tyr, Trp or Phe
<220> FEATURE:
<221> NAME/KEY: variant
<222> LOCATION: (16)
<223> OTHER INFORMATION: Leu
<220> FEATURE:
<221> NAME/KEY: variant
<222> LOCATION: (17)
<223> OTHER INFORMATION: Ser, Pro, Phe, Leu or Ile
<220> FEATURE:
<221> NAME/KEY: variant
<222> LOCATION: (18)
<223> OTHER INFORMATION: Ala, Thr, Glu, Gln, Val, Pro or Ser
<220> FEATURE:
<221> NAME/KEY: variant
<222> LOCATION: (19)
<223> OTHER INFORMATION: Glu, Lys, Gln, Asp or Asn
<220> FEATURE:
<221> NAME/KEY: variant
<222> LOCATION: (20)
<223> OTHER INFORMATION: Pro, Ser Ala or Asn
<220> FEATURE:
<221> NAME/KEY: variant
<222> LOCATION: (21)
<223> OTHER INFORMATION: Val, Asn, Gly or Pro
<220> FEATURE:
<221> NAME/KEY: variant
<222> LOCATION: (22)
<223> OTHER INFORMATION: Pro, Gln, His, Ser, Leu Arg, Thr, Asp or Ile
<220> FEATURE:
<221> NAME/KEY: variant
<222> LOCATION: (23)
<223> OTHER INFORMATION: Leu, Phe or Val
<220> FEATURE:
<221> NAME/KEY: variant
<222> LOCATION: (24)
<223> OTHER INFORMATION: Gln, Leu, Pro, His, Asp or Glu
<220> FEATURE:
<221> NAME/KEY: variant
<222> LOCATION: (25)
<223> OTHER INFORMATION: Leu
<220> FEATURE:
<221> NAME/KEY: variant
<222> LOCATION: (26)
```

```
<223> OTHER INFORMATION: Pro
<220> FEATURE:
<221> NAME/KEY: variant
<222> LOCATION: (27)
<223> OTHER INFORMATION: Pro
<220> FEATURE:
<221> NAME/KEY: variant
<222> LOCATION: (28)
<223> OTHER INFORMATION: Leu
<220> FEATURE:
<223> OTHER INFORMATION: Description of Artificial Sequence: SYNTHETIC
      CONSTRUCT

<400> SEQUENCE: 7

Xaa Ile Leu Xaa Xaa Xaa Leu Gly Arg Xaa Xaa Xaa Xaa Xaa Leu Xaa Xaa
 1               5                  10                  15

Xaa Xaa Xaa Xaa Xaa Xaa Leu Pro Pro Leu
        20                  25

<210> SEQ ID NO 8
<211> LENGTH: 28
<212> TYPE: PRT
<213> ORGANISM: Artificial Sequence
<220> FEATURE:
<221> NAME/KEY: variant
<222> LOCATION: (1)
<223> OTHER INFORMATION: Arg
<220> FEATURE:
<221> NAME/KEY: variant
<222> LOCATION: (2)
<223> OTHER INFORMATION: Ile
<220> FEATURE:
<221> NAME/KEY: variant
<222> LOCATION: (3)
<223> OTHER INFORMATION: Leu
<220> FEATURE:
<221> NAME/KEY: variant
<222> LOCATION: (4)
<223> OTHER INFORMATION: Ser
<220> FEATURE:
<221> NAME/KEY: variant
<222> LOCATION: (5)
<223> OTHER INFORMATION: Thr
<220> FEATURE:
<221> NAME/KEY: variant
<222> LOCATION: (6)
<223> OTHER INFORMATION: Tyr
<220> FEATURE:
<221> NAME/KEY: variant
<222> LOCATION: (7)
<223> OTHER INFORMATION: Leu
<220> FEATURE:
<221> NAME/KEY: variant
<222> LOCATION: (8)
<223> OTHER INFORMATION: Gly
<220> FEATURE:
<221> NAME/KEY: variant
<222> LOCATION: (9)
<223> OTHER INFORMATION: Arg
<220> FEATURE:
<221> NAME/KEY: variant
<222> LOCATION: (10)
<223> OTHER INFORMATION: Ile
<220> FEATURE:
<221> NAME/KEY: variant
<222> LOCATION: (11)
<223> OTHER INFORMATION: Ser
<220> FEATURE:
<221> NAME/KEY: variant
<222> LOCATION: (12)
<223> OTHER INFORMATION: Gly
<220> FEATURE:
<221> NAME/KEY: variant
<222> LOCATION: (13)
<223> OTHER INFORMATION: Gly
<220> FEATURE:
```

```
<221> NAME/KEY: variant
<222> LOCATION: (14)
<223> OTHER INFORMATION: Gly
<220> FEATURE:
<221> NAME/KEY: variant
<222> LOCATION: (15)
<223> OTHER INFORMATION: Trp
<220> FEATURE:
<221> NAME/KEY: variant
<222> LOCATION: (16)
<223> OTHER INFORMATION: Leu
<220> FEATURE:
<221> NAME/KEY: variant
<222> LOCATION: (17)
<223> OTHER INFORMATION: Ser
<220> FEATURE:
<221> NAME/KEY: variant
<222> LOCATION: (18)
<223> OTHER INFORMATION: Ala
<220> FEATURE:
<221> NAME/KEY: variant
<222> LOCATION: (19)
<223> OTHER INFORMATION: Glu
<220> FEATURE:
<221> NAME/KEY: variant
<222> LOCATION: (20)
<223> OTHER INFORMATION: Pro
<220> FEATURE:
<221> NAME/KEY: variant
<222> LOCATION: (21)
<223> OTHER INFORMATION: Val
<220> FEATURE:
<221> NAME/KEY: variant
<222> LOCATION: (22)
<223> OTHER INFORMATION: Pro
<220> FEATURE:
<221> NAME/KEY: variant
<222> LOCATION: (23)
<223> OTHER INFORMATION: Leu
<220> FEATURE:
<221> NAME/KEY: variant
<222> LOCATION: (24)
<223> OTHER INFORMATION: Gln
<220> FEATURE:
<221> NAME/KEY: variant
<222> LOCATION: (25)
<223> OTHER INFORMATION: Leu
<220> FEATURE:
<221> NAME/KEY: variant
<222> LOCATION: (26)
<223> OTHER INFORMATION: Pro
<220> FEATURE:
<221> NAME/KEY: variant
<222> LOCATION: (27)
<223> OTHER INFORMATION: Pro
<220> FEATURE:
<221> NAME/KEY: variant
<222> LOCATION: (28)
<223> OTHER INFORMATION: Leu
<220> FEATURE:
<223> OTHER INFORMATION: Description of Artificial Sequence: SYNTHETIC
      CONSTRUCT

<400> SEQUENCE: 8

Arg Ile Leu Ser Thr Tyr Leu Gly Arg Ile Ser Gly Gly Gly Trp Leu Ser Ala
  1               5                  10                  15

Glu Pro Val Pro Leu Gln Leu Pro Pro Leu
     20                  25

<210> SEQ ID NO 9
<211> LENGTH: 28
<212> TYPE: PRT
<213> ORGANISM: Artificial Sequence
<220> FEATURE:
<221> NAME/KEY: variant
<222> LOCATION: (1)
```

```
<223> OTHER INFORMATION: Arg
<220> FEATURE:
<221> NAME/KEY: variant
<222> LOCATION: (2)
<223> OTHER INFORMATION: Ile
<220> FEATURE:
<221> NAME/KEY: variant
<222> LOCATION: (3)
<223> OTHER INFORMATION: Leu
<220> FEATURE:
<221> NAME/KEY: variant
<222> LOCATION: (4)
<223> OTHER INFORMATION: Ser
<220> FEATURE:
<221> NAME/KEY: variant
<222> LOCATION: (5)
<223> OTHER INFORMATION: Thr
<220> FEATURE:
<221> NAME/KEY: variant
<222> LOCATION: (6)
<223> OTHER INFORMATION: Tyr
<220> FEATURE:
<221> NAME/KEY: variant
<222> LOCATION: (7)
<223> OTHER INFORMATION: Leu
<220> FEATURE:
<221> NAME/KEY: variant
<222> LOCATION: (8)
<223> OTHER INFORMATION: Gly
<220> FEATURE:
<221> NAME/KEY: variant
<222> LOCATION: (9)
<223> OTHER INFORMATION: Arg
<220> FEATURE:
<221> NAME/KEY: variant
<222> LOCATION: (10)
<223> OTHER INFORMATION: Ile
<220> FEATURE:
<221> NAME/KEY: variant
<222> LOCATION: (11)
<223> OTHER INFORMATION: Ser
<220> FEATURE:
<221> NAME/KEY: variant
<222> LOCATION: (12)
<223> OTHER INFORMATION: Gly
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Gly
<220> FEATURE:
<221> NAME/KEY: variant
<222> LOCATION: (15)
<223> OTHER INFORMATION: Tyr
<220> FEATURE:
<221> NAME/KEY: variant
<222> LOCATION: (16)
<223> OTHER INFORMATION: Leu
<220> FEATURE:
<221> NAME/KEY: variant
<222> LOCATION: (17)
<223> OTHER INFORMATION: Ser
<220> FEATURE:
<221> NAME/KEY: variant
<222> LOCATION: (18)
<223> OTHER INFORMATION: Ala
<220> FEATURE:
<221> NAME/KEY: variant
<222> LOCATION: (19)
<223> OTHER INFORMATION: Glu
<220> FEATURE:
<221> NAME/KEY: variant
<222> LOCATION: (20)
<223> OTHER INFORMATION: Pro
<220> FEATURE:
<221> NAME/KEY: variant
```

```
<222> LOCATION: (21)
<223> OTHER INFORMATION: Val
<220> FEATURE:
<221> NAME/KEY: variant
<222> LOCATION: (22)
<223> OTHER INFORMATION: Pro
<220> FEATURE:
<221> NAME/KEY: variant
<222> LOCATION: (23)
<223> OTHER INFORMATION: Leu
<220> FEATURE:
<221> NAME/KEY: variant
<222> LOCATION: (24)
<223> OTHER INFORMATION: Gln
<220> FEATURE:
<221> NAME/KEY: variant
<222> LOCATION: (25)
<223> OTHER INFORMATION: Leu
<220> FEATURE:
<221> NAME/KEY: variant
<222> LOCATION: (26)
<223> OTHER INFORMATION: Pro
<220> FEATURE:
<221> NAME/KEY: variant
<222> LOCATION: (27)
<223> OTHER INFORMATION: Pro
<220> FEATURE:
<221> NAME/KEY: variant
<222> LOCATION: (28)
<223> OTHER INFORMATION: Leu
<220> FEATURE:
<223> OTHER INFORMATION: Description of Artificial Sequence: SYNTHETIC
      CONSTRUCT

<400> SEQUENCE: 9

Arg Ile Leu Ser Thr Tyr Leu Gly Arg Ile Ser Gly Gly Gly Tyr Leu Ser Ala
 1               5                  10                  15

Glu Pro Val Pro Leu Gln Leu Pro Pro Leu
    20                  25

<210> SEQ ID NO 10
<211> LENGTH: 28
<212> TYPE: PRT
<213> ORGANISM: Artificial Sequence
<220> FEATURE:
<221> NAME/KEY: variant
<222> LOCATION: (1)
<223> OTHER INFORMATION: Lys or Arg
<220> FEATURE:
<221> NAME/KEY: variant
<222> LOCATION: (2)
<223> OTHER INFORMATION: Leu
<220> FEATURE:
<221> NAME/KEY: variant
<222> LOCATION: (3)
<223> OTHER INFORMATION: Val
<220> FEATURE:
<221> NAME/KEY: variant
<222> LOCATION: (4)
<223> OTHER INFORMATION: Gly
<220> FEATURE:
<221> NAME/KEY: variant
<222> LOCATION: (5)
<223> OTHER INFORMATION: Phe or Leu
<220> FEATURE:
<221> NAME/KEY: variant
<222> LOCATION: (6)
<223> OTHER INFORMATION: Pro
<220> FEATURE:
<221> NAME/KEY: variant
<222> LOCATION: (7)
<223> OTHER INFORMATION: 1390:<223  Ile or Val
<220> FEATURE:
<221> NAME/KEY: variant
<222> LOCATION: (8)
<223> OTHER INFORMATION: Thr, Arg, Lys, Ala or Met
```

-continued

```
<220> FEATURE:
<221> NAME/KEY: variant
<222> LOCATION: (9)
<223> OTHER INFORMATION: Pro
<220> FEATURE:
<221> NAME/KEY: variant
<222> LOCATION: (10)
<223> OTHER INFORMATION: Gln or His
<220> FEATURE:
<221> NAME/KEY: variant
<222> LOCATION: (11)
<223> OTHER INFORMATION: Val, Leu or Ile
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Gly or None or PEG linker
<220> FEATURE:
<221> NAME/KEY: variant
<222> LOCATION: (14)
<223> OTHER INFORMATION: Gly or None or PEG linker
<220> FEATURE:
<221> NAME/KEY: variant
<222> LOCATION: (15)
<223> OTHER INFORMATION: Gly or None or PEG linker
<220> FEATURE:
<221> NAME/KEY: variant
<222> LOCATION: (16)
<223> OTHER INFORMATION: Arg or None
<220> FEATURE:
<221> NAME/KEY: variant
<222> LOCATION: (17)
<223> OTHER INFORMATION: Arg or None
<220> FEATURE:
<221> NAME/KEY: variant
<222> LOCATION: (18)
<223> OTHER INFORMATION: Arg or None
<220> FEATURE:
<221> NAME/KEY: variant
<222> LOCATION: (19)
<223> OTHER INFORMATION: Leu
<220> FEATURE:
<221> NAME/KEY: variant
<222> LOCATION: (20)
<223> OTHER INFORMATION: Leu, Val or Thr
<220> FEATURE:
<221> NAME/KEY: variant
<222> LOCATION: (21)
<223> OTHER INFORMATION: Arg or Cit
<220> FEATURE:
<221> NAME/KEY: variant
<222> LOCATION: (22)
<223> OTHER INFORMATION: Pro
<220> FEATURE:
<221> NAME/KEY: variant
<222> LOCATION: (23)
<223> OTHER INFORMATION: Met, Val, Ile, Leu or Nle
<220> FEATURE:
<221> NAME/KEY: variant
<222> LOCATION: (24)
<223> OTHER INFORMATION: Thr or Asp
<220> FEATURE:
<221> NAME/KEY: variant
<222> LOCATION: (25)
<223> OTHER INFORMATION: Tyr, Phe or Arg
<220> FEATURE:
<221> NAME/KEY: variant
<222> LOCATION: (26)
<223> OTHER INFORMATION: Lys or Arg
<220> FEATURE:
<221> NAME/KEY: variant
<222> LOCATION: (27)
<223> OTHER INFORMATION: Ala, Gly, Ser, Glu or Gln
<220> FEATURE:
<221> NAME/KEY: variant
<222> LOCATION: (28)
```

-continued

```
<223> OTHER INFORMATION: Ala, Ser or Val
<220> FEATURE:
<223> OTHER INFORMATION: Description of Artificial Sequence: SYNTHETIC
      CONSTRUCT

<400> SEQUENCE: 10

Xaa Leu Val Gly Xaa Pro Xaa Xaa Pro Xaa Xaa Pro Xaa Xaa Xaa Xaa
 1               5                   10                  15

Xaa Xaa Leu Xaa Xaa Pro Xaa Xaa Xaa Xaa Xaa Xaa
            20                  25

<210> SEQ ID NO 11
<211> LENGTH: 26
<212> TYPE: PRT
<213> ORGANISM: Artificial Sequence
<220> FEATURE:
<221> NAME/KEY: variant
<222> LOCATION: (1)
<223> OTHER INFORMATION: Lys
<220> FEATURE:
<221> NAME/KEY: variant
<222> LOCATION: (2)
<223> OTHER INFORMATION: Leu
<220> FEATURE:
<221> NAME/KEY: variant
<222> LOCATION: (3)
<223> OTHER INFORMATION: Val
<220> FEATURE:
<221> NAME/KEY: variant
<222> LOCATION: (4)
<223> OTHER INFORMATION: Gly
<220> FEATURE:
<221> NAME/KEY: variant
<222> LOCATION: (5)
<223> OTHER INFORMATION: Phe
<220> FEATURE:
<221> NAME/KEY: variant
<222> LOCATION: (6)
<223> OTHER INFORMATION: Pro
<220> FEATURE:
<221> NAME/KEY: variant
<222> LOCATION: (7)
<223> OTHER INFORMATION: 1547:<223 Val
<220> FEATURE:
<221> NAME/KEY: variant
<222> LOCATION: (8)
<223> OTHER INFORMATION: Lys
<220> FEATURE:
<221> NAME/KEY: variant
<222> LOCATION: (9)
<223> OTHER INFORMATION: Pro
<220> FEATURE:
<221> NAME/KEY: variant
<222> LOCATION: (10)
<223> OTHER INFORMATION: Gln
<220> FEATURE:
<221> NAME/KEY: variant
<222> LOCATION: (11)
<223> OTHER INFORMATION: Val
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Gly
<220> FEATURE:
<221> NAME/KEY: variant
<222> LOCATION: (15)
<223> OTHER INFORMATION: Gly
<220> FEATURE:
```

```
<221> NAME/KEY: variant
<222> LOCATION: (16)
<223> OTHER INFORMATION: Arg
<220> FEATURE:
<221> NAME/KEY: variant
<222> LOCATION: (17)
<223> OTHER INFORMATION: Leu
<220> FEATURE:
<221> NAME/KEY: variant
<222> LOCATION: (18)
<223> OTHER INFORMATION: Leu
<220> FEATURE:
<221> NAME/KEY: variant
<222> LOCATION: (19)
<223> OTHER INFORMATION: Cit
<220> FEATURE:
<221> NAME/KEY: variant
<222> LOCATION: (20)
<223> OTHER INFORMATION: Pro
<220> FEATURE:
<221> NAME/KEY: variant
<222> LOCATION: (21)
<223> OTHER INFORMATION: Nle
<220> FEATURE:
<221> NAME/KEY: variant
<222> LOCATION: (22)
<223> OTHER INFORMATION: Thr
<220> FEATURE:
<221> NAME/KEY: variant
<222> LOCATION: (23)
<223> OTHER INFORMATION: Tyr
<220> FEATURE:
<221> NAME/KEY: variant
<222> LOCATION: (24)
<223> OTHER INFORMATION: Lys
<220> FEATURE:
<221> NAME/KEY: variant
<222> LOCATION: (25)
<223> OTHER INFORMATION: Ala
<220> FEATURE:
<221> NAME/KEY: variant
<222> LOCATION: (26)
<223> OTHER INFORMATION: Ala
<220> FEATURE:
<223> OTHER INFORMATION: Description of Artificial Sequence: SYNTHETIC
      CONSTRUCT

<400> SEQUENCE: 11

Lys Leu Val Gly Phe Pro Val Lys Pro Gln Val Pro Gly Gly Gly Arg Leu Leu
 1               5                  10                  15

Xaa Pro Xaa Thr Tyr Lys Ala Ala
        20                  25

<210> SEQ ID NO 12
<211> LENGTH: 26
<212> TYPE: PRT
<213> ORGANISM: Artificial Sequence
<220> FEATURE:
<221> NAME/KEY: variant
<222> LOCATION: (1)
<223> OTHER INFORMATION: Arg
<220> FEATURE:
<221> NAME/KEY: variant
<222> LOCATION: (2)
<223> OTHER INFORMATION: Leu
<220> FEATURE:
<221> NAME/KEY: variant
<222> LOCATION: (3)
<223> OTHER INFORMATION: Val
<220> FEATURE:
<221> NAME/KEY: variant
<222> LOCATION: (4)
<223> OTHER INFORMATION: Gly
<220> FEATURE:
<221> NAME/KEY: variant
<222> LOCATION: (5)
```

```
<223> OTHER INFORMATION: Phe
<220> FEATURE:
<221> NAME/KEY: variant
<222> LOCATION: (6)
<223> OTHER INFORMATION: Pro
<220> FEATURE:
<221> NAME/KEY: variant
<222> LOCATION: (7)
<223> OTHER INFORMATION: 1694:<223 Val
<220> FEATURE:
<221> NAME/KEY: variant
<222> LOCATION: (8)
<223> OTHER INFORMATION: Lys
<220> FEATURE:
<221> NAME/KEY: variant
<222> LOCATION: (9)
<223> OTHER INFORMATION: Pro
<220> FEATURE:
<221> NAME/KEY: variant
<222> LOCATION: (10)
<223> OTHER INFORMATION: Gln
<220> FEATURE:
<221> NAME/KEY: variant
<222> LOCATION: (11)
<223> OTHER INFORMATION: Val
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Gly
<220> FEATURE:
<221> NAME/KEY: variant
<222> LOCATION: (15)
<223> OTHER INFORMATION: Gly
<220> FEATURE:
<221> NAME/KEY: variant
<222> LOCATION: (16)
<223> OTHER INFORMATION: Arg
<220> FEATURE:
<221> NAME/KEY: variant
<222> LOCATION: (17)
<223> OTHER INFORMATION: Leu
<220> FEATURE:
<221> NAME/KEY: variant
<222> LOCATION: (18)
<223> OTHER INFORMATION: Leu
<220> FEATURE:
<221> NAME/KEY: variant
<222> LOCATION: (19)
<223> OTHER INFORMATION: Arg
<220> FEATURE:
<221> NAME/KEY: variant
<222> LOCATION: (20)
<223> OTHER INFORMATION: Pro
<220> FEATURE:
<221> NAME/KEY: variant
<222> LOCATION: (21)
<223> OTHER INFORMATION: Leu
<220> FEATURE:
<221> NAME/KEY: variant
<222> LOCATION: (22)
<223> OTHER INFORMATION: Thr
<220> FEATURE:
<221> NAME/KEY: variant
<222> LOCATION: (23)
<223> OTHER INFORMATION: Tyr
<220> FEATURE:
<221> NAME/KEY: variant
<222> LOCATION: (24)
<223> OTHER INFORMATION: Lys
<220> FEATURE:
<221> NAME/KEY: variant
```

```
<222> LOCATION: (25)
<223> OTHER INFORMATION: Ala
<220> FEATURE:
<221> NAME/KEY: variant
<222> LOCATION: (26)
<223> OTHER INFORMATION: Ala
<220> FEATURE:
<223> OTHER INFORMATION: Description of Artificial Sequence: SYNTHETIC
      CONSTRUCT

<400> SEQUENCE: 12

Arg Leu Val Gly Phe Pro Val Lys Pro Gln Val Pro Gly Gly Gly Arg Leu Leu
 1               5                  10                  15

Arg Pro Leu Thr Tyr Lys Ala Ala
        20                  25

<210> SEQ ID NO 13
<211> LENGTH: 22
<212> TYPE: PRT
<213> ORGANISM: Artificial Sequence
<220> FEATURE:
<221> NAME/KEY: variant
<222> LOCATION: (1)
<223> OTHER INFORMATION: Phe
<220> FEATURE:
<221> NAME/KEY: variant
<222> LOCATION: (2)
<223> OTHER INFORMATION: Val
<220> FEATURE:
<221> NAME/KEY: variant
<222> LOCATION: (3)
<223> OTHER INFORMATION: Ile
<220> FEATURE:
<221> NAME/KEY: variant
<222> LOCATION: (4)
<223> OTHER INFORMATION: Pro
<220> FEATURE:
<221> NAME/KEY: variant
<222> LOCATION: (5)
<223> OTHER INFORMATION: Arg
<220> FEATURE:
<221> NAME/KEY: variant
<222> LOCATION: (6)
<223> OTHER INFORMATION: Leu
<220> FEATURE:
<221> NAME/KEY: variant
<222> LOCATION: (7)
<223> OTHER INFORMATION: 1841:<223 Glu
<220> FEATURE:
<221> NAME/KEY: variant
<222> LOCATION: (8)
<223> OTHER INFORMATION: Pro
<220> FEATURE:
<221> NAME/KEY: variant
<222> LOCATION: (9)
<223> OTHER INFORMATION: Trp
<220> FEATURE:
<221> NAME/KEY: variant
<222> LOCATION: (10)
<223> OTHER INFORMATION: Nle
<220> FEATURE:
<221> NAME/KEY: variant
<222> LOCATION: (11)
<223> OTHER INFORMATION: His
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Ser
```

```
<220> FEATURE:
<221> NAME/KEY: variant
<222> LOCATION: (15)
<223> OTHER INFORMATION: Gln
<220> FEATURE:
<221> NAME/KEY: variant
<222> LOCATION: (16)
<223> OTHER INFORMATION: Pro
<220> FEATURE:
<221> NAME/KEY: variant
<222> LOCATION: (17)
<223> OTHER INFORMATION: Nle
<220> FEATURE:
<221> NAME/KEY: variant
<222> LOCATION: (18)
<223> OTHER INFORMATION: Thr
<220> FEATURE:
<221> NAME/KEY: variant
<222> LOCATION: (19)
<223> OTHER INFORMATION: Ala
<220> FEATURE:
<221> NAME/KEY: variant
<222> LOCATION: (20)
<223> OTHER INFORMATION: Cys
<220> FEATURE:
<221> NAME/KEY: variant
<222> LOCATION: (21)
<223> OTHER INFORMATION: Thr
<220> FEATURE:
<221> NAME/KEY: variant
<222> LOCATION: (22)
<223> OTHER INFORMATION: Asn
<220> FEATURE:
<223> OTHER INFORMATION: Description of Artificial Sequence: SYNTHETIC
      CONSTRUCT

<400> SEQUENCE: 13

Phe Val Ile Pro Arg Leu Glu Pro Trp Xaa His Pro Gly Ser Gln Pro Xaa Thr
  1               5                  10                  15

Ala Cys Thr Asn
     20

<210> SEQ ID NO 14
<211> LENGTH: 22
<212> TYPE: PRT
<213> ORGANISM: Artificial Sequence
<220> FEATURE:
<221> NAME/KEY: variant
<222> LOCATION: (1)
<223> OTHER INFORMATION: Phe
<220> FEATURE:
<221> NAME/KEY: variant
<222> LOCATION: (2)
<223> OTHER INFORMATION: Val
<220> FEATURE:
<221> NAME/KEY: variant
<222> LOCATION: (3)
<223> OTHER INFORMATION: Ile
<220> FEATURE:
<221> NAME/KEY: variant
<222> LOCATION: (4)
<223> OTHER INFORMATION: His
<220> FEATURE:
<221> NAME/KEY: variant
<222> LOCATION: (5)
<223> OTHER INFORMATION: Arg
<220> FEATURE:
<221> NAME/KEY: variant
<222> LOCATION: (6)
<223> OTHER INFORMATION: Leu
<220> FEATURE:
<221> NAME/KEY: variant
<222> LOCATION: (7)
<223> OTHER INFORMATION: 1969:<223 Glu
<220> FEATURE:
<221> NAME/KEY: variant
```

```
<222> LOCATION: (8)
<223> OTHER INFORMATION: Pro
<220> FEATURE:
<221> NAME/KEY: variant
<222> LOCATION: (9)
<223> OTHER INFORMATION: Trp
<220> FEATURE:
<221> NAME/KEY: variant
<222> LOCATION: (10)
<223> OTHER INFORMATION: Leu
<220> FEATURE:
<221> NAME/KEY: variant
<222> LOCATION: (11)
<223> OTHER INFORMATION: His
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Ser
<220> FEATURE:
<221> NAME/KEY: variant
<222> LOCATION: (15)
<223> OTHER INFORMATION: Gln
<220> FEATURE:
<221> NAME/KEY: variant
<222> LOCATION: (16)
<223> OTHER INFORMATION: Pro
<220> FEATURE:
<221> NAME/KEY: variant
<222> LOCATION: (17)
<223> OTHER INFORMATION: Nle
<220> FEATURE:
<221> NAME/KEY: variant
<222> LOCATION: (18)
<223> OTHER INFORMATION: Thr
<220> FEATURE:
<221> NAME/KEY: variant
<222> LOCATION: (19)
<223> OTHER INFORMATION: Ala
<220> FEATURE:
<221> NAME/KEY: variant
<222> LOCATION: (20)
<223> OTHER INFORMATION: Ser
<220> FEATURE:
<221> NAME/KEY: variant
<222> LOCATION: (21)
<223> OTHER INFORMATION: Thr
<220> FEATURE:
<221> NAME/KEY: variant
<222> LOCATION: (22)
<223> OTHER INFORMATION: Asn
<220> FEATURE:
<223> OTHER INFORMATION: Description of Artificial Sequence: SYNTHETIC
      CONSTRUCT

<400> SEQUENCE: 14

Phe Val Ile His Arg Leu Glu Pro Trp Leu His Pro Gly Ser Gln His Xaa Thr
  1               5                  10                  15

Ala Ser Thr Asn
        20

<210> SEQ ID NO 15
<211> LENGTH: 23
<212> TYPE: PRT
<213> ORGANISM: Artificial Sequence
<220> FEATURE:
<221> NAME/KEY: variant
<222> LOCATION: (1)
<223> OTHER INFORMATION: Arg
```

-continued

```
<220> FEATURE:
<221> NAME/KEY: variant
<222> LOCATION: (2)
<223> OTHER INFORMATION: Leu
<220> FEATURE:
<221> NAME/KEY: variant
<222> LOCATION: (3)
<223> OTHER INFORMATION: Val
<220> FEATURE:
<221> NAME/KEY: variant
<222> LOCATION: (4)
<223> OTHER INFORMATION: Gly
<220> FEATURE:
<221> NAME/KEY: variant
<222> LOCATION: (5)
<223> OTHER INFORMATION: Phe
<220> FEATURE:
<221> NAME/KEY: variant
<222> LOCATION: (6)
<223> OTHER INFORMATION: Pro
<220> FEATURE:
<221> NAME/KEY: variant
<222> LOCATION: (7)
<223> OTHER INFORMATION: 2096:<223 Val
<220> FEATURE:
<221> NAME/KEY: variant
<222> LOCATION: (8)
<223> OTHER INFORMATION: Lys
<220> FEATURE:
<221> NAME/KEY: variant
<222> LOCATION: (9)
<223> OTHER INFORMATION: Pro
<220> FEATURE:
<221> NAME/KEY: variant
<222> LOCATION: (10)
<223> OTHER INFORMATION: Gln
<220> FEATURE:
<221> NAME/KEY: variant
<222> LOCATION: (11)
<223> OTHER INFORMATION: Val
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Gly
<220> FEATURE:
<221> NAME/KEY: variant
<222> LOCATION: (14)
<223> OTHER INFORMATION: Leu
<220> FEATURE:
<221> NAME/KEY: variant
<222> LOCATION: (15)
<223> OTHER INFORMATION: Leu
<220> FEATURE:
<221> NAME/KEY: variant
<222> LOCATION: (16)
<223> OTHER INFORMATION: Arg
<220> FEATURE:
<221> NAME/KEY: variant
<222> LOCATION: (17)
<223> OTHER INFORMATION: Pro
<220> FEATURE:
<221> NAME/KEY: variant
<222> LOCATION: (18)
<223> OTHER INFORMATION: Leu
<220> FEATURE:
<221> NAME/KEY: variant
<222> LOCATION: (19)
<223> OTHER INFORMATION: Thr
<220> FEATURE:
<221> NAME/KEY: variant
<222> LOCATION: (20)
<223> OTHER INFORMATION: Tyr
<220> FEATURE:
<221> NAME/KEY: variant
<222> LOCATION: (21)
```

```
<223> OTHER INFORMATION: Lys
<220> FEATURE:
<221> NAME/KEY: variant
<222> LOCATION: (22)
<223> OTHER INFORMATION: Ala
<220> FEATURE:
<221> NAME/KEY: variant
<222> LOCATION: (23)
<223> OTHER INFORMATION: Ala
<220> FEATURE:
<223> OTHER INFORMATION: Description of Artificial Sequence: SYNTHETIC
      CONSTRUCT

<400> SEQUENCE: 15

Arg Leu Val Gly Phe Pro Val Lys Pro Gln Val Pro Gly Leu Leu Arg Pro Leu
  1               5                  10                  15

Thr Tyr Lys Ala Ala
        20

<210> SEQ ID NO 16
<211> LENGTH: 24
<212> TYPE: PRT
<213> ORGANISM: Artificial Sequence
<220> FEATURE:
<221> NAME/KEY: variant
<222> LOCATION: (1)
<223> OTHER INFORMATION: Met
<220> FEATURE:
<221> NAME/KEY: variant
<222> LOCATION: (2)
<223> OTHER INFORMATION: Glu
<220> FEATURE:
<221> NAME/KEY: variant
<222> LOCATION: (3)
<223> OTHER INFORMATION: Ser
<220> FEATURE:
<221> NAME/KEY: variant
<222> LOCATION: (4)
<223> OTHER INFORMATION: Val
<220> FEATURE:
<221> NAME/KEY: variant
<222> LOCATION: (5)
<223> OTHER INFORMATION: Asp
<220> FEATURE:
<221> NAME/KEY: variant
<222> LOCATION: (6)
<223> OTHER INFORMATION: Pro
<220> FEATURE:
<221> NAME/KEY: variant
<222> LOCATION: (7)
<223> OTHER INFORMATION: 2228:<223 Arg
<220> FEATURE:
<221> NAME/KEY: variant
<222> LOCATION: (8)
<223> OTHER INFORMATION: Leu
<220> FEATURE:
<221> NAME/KEY: variant
<222> LOCATION: (9)
<223> OTHER INFORMATION: Glu
<220> FEATURE:
<221> NAME/KEY: variant
<222> LOCATION: (10)
<223> OTHER INFORMATION: Pro
<220> FEATURE:
<221> NAME/KEY: variant
<222> LOCATION: (11)
<223> OTHER INFORMATION: Trp
<220> FEATURE:
<221> NAME/KEY: variant
<222> LOCATION: (12)
<223> OTHER INFORMATION: Lys
<220> FEATURE:
<221> NAME/KEY: variant
<222> LOCATION: (13)
<223> OTHER INFORMATION: His
<220> FEATURE:
```

```
<221> NAME/KEY: variant
<222> LOCATION: (14)
<223> OTHER INFORMATION: Pro
<220> FEATURE:
<221> NAME/KEY: variant
<222> LOCATION: (15)
<223> OTHER INFORMATION: Gly
<220> FEATURE:
<221> NAME/KEY: variant
<222> LOCATION: (16)
<223> OTHER INFORMATION: Ser
<220> FEATURE:
<221> NAME/KEY: variant
<222> LOCATION: (17)
<223> OTHER INFORMATION: Gln
<220> FEATURE:
<221> NAME/KEY: variant
<222> LOCATION: (18)
<223> OTHER INFORMATION: Pro
<220> FEATURE:
<221> NAME/KEY: variant
<222> LOCATION: (19)
<223> OTHER INFORMATION: Lys
<220> FEATURE:
<221> NAME/KEY: variant
<222> LOCATION: (20)
<223> OTHER INFORMATION: Thr
<220> FEATURE:
<221> NAME/KEY: variant
<222> LOCATION: (21)
<223> OTHER INFORMATION: Ala
<220> FEATURE:
<221> NAME/KEY: variant
<222> LOCATION: (22)
<223> OTHER INFORMATION: Cys
<220> FEATURE:
<221> NAME/KEY: variant
<222> LOCATION: (23)
<223> OTHER INFORMATION: Thr
<220> FEATURE:
<221> NAME/KEY: variant
<222> LOCATION: (24)
<223> OTHER INFORMATION: Asn
<220> FEATURE:
<223> OTHER INFORMATION: Description of Artificial Sequence: SYNTHETIC
      CONSTRUCT

<400> SEQUENCE: 16

Met Glu Ser Val Asp Pro Arg Leu Glu Pro Trp Lys His Pro Gly Ser Gln Pro
 1               5                  10                  15

Lys Thr Ala Cys Thr Asn
     20

<210> SEQ ID NO 17
<211> LENGTH: 23
<212> TYPE: PRT
<213> ORGANISM: Artificial Sequence
<220> FEATURE:
<221> NAME/KEY: variant
<222> LOCATION: (1)
<223> OTHER INFORMATION: Gln
<220> FEATURE:
<221> NAME/KEY: variant
<222> LOCATION: (2)
<223> OTHER INFORMATION: Val
<220> FEATURE:
<221> NAME/KEY: variant
<222> LOCATION: (3)
<223> OTHER INFORMATION: Cys
<220> FEATURE:
<221> NAME/KEY: variant
<222> LOCATION: (4)
<223> OTHER INFORMATION: Phe
<220> FEATURE:
<221> NAME/KEY: variant
<222> LOCATION: (5)
```

```
<223> OTHER INFORMATION: Ile
<220> FEATURE:
<221> NAME/KEY: variant
<222> LOCATION: (6)
<223> OTHER INFORMATION: Thr
<220> FEATURE:
<221> NAME/KEY: variant
<222> LOCATION: (7)
<223> OTHER INFORMATION: 2365:<223 Lys
<220> FEATURE:
<221> NAME/KEY: variant
<222> LOCATION: (8)
<223> OTHER INFORMATION: Gly
<220> FEATURE:
<221> NAME/KEY: variant
<222> LOCATION: (9)
<223> OTHER INFORMATION: Leu
<220> FEATURE:
<221> NAME/KEY: variant
<222> LOCATION: (10)
<223> OTHER INFORMATION: Gly
<220> FEATURE:
<221> NAME/KEY: variant
<222> LOCATION: (11)
<223> OTHER INFORMATION: Ile
<220> FEATURE:
<221> NAME/KEY: variant
<222> LOCATION: (12)
<223> OTHER INFORMATION: Ser
<220> FEATURE:
<221> NAME/KEY: variant
<222> LOCATION: (13)
<223> OTHER INFORMATION: Tyr
<220> FEATURE:
<221> NAME/KEY: variant
<222> LOCATION: (14)
<223> OTHER INFORMATION: Gly
<220> FEATURE:
<221> NAME/KEY: variant
<222> LOCATION: (15)
<223> OTHER INFORMATION: Arg
<220> FEATURE:
<221> NAME/KEY: variant
<222> LOCATION: (16)
<223> OTHER INFORMATION: Lys
<220> FEATURE:
<221> NAME/KEY: variant
<222> LOCATION: (17)
<223> OTHER INFORMATION: Lys
<220> FEATURE:
<221> NAME/KEY: variant
<222> LOCATION: (18)
<223> OTHER INFORMATION: Arg
<220> FEATURE:
<221> NAME/KEY: variant
<222> LOCATION: (19)
<223> OTHER INFORMATION: Arg
<220> FEATURE:
<221> NAME/KEY: variant
<222> LOCATION: (20)
<223> OTHER INFORMATION: Gln
<220> FEATURE:
<221> NAME/KEY: variant
<222> LOCATION: (21)
<223> OTHER INFORMATION: Arg
<220> FEATURE:
<221> NAME/KEY: variant
<222> LOCATION: (22)
<223> OTHER INFORMATION: Arg
<220> FEATURE:
<221> NAME/KEY: variant
<222> LOCATION: (23)
<223> OTHER INFORMATION: Arg
<220> FEATURE:
<223> OTHER INFORMATION: Description of Artificial Sequence: SYNTHETIC
      CONSTRUCT

<400> SEQUENCE: 17
```

Gln Val Cys Phe Ile Thr Lys Gly Leu Gly Ile Ser Tyr Gly Arg Lys Lys Arg
1               5                   10                  15

Arg Gln Arg Arg Arg
    20

<210> SEQ ID NO 18
<211> LENGTH: 21
<212> TYPE: PRT
<213> ORGANISM: Artificial Sequence
<220> FEATURE:
<221> NAME/KEY: variant
<222> LOCATION: (1)
<223> OTHER INFORMATION: Glu
<220> FEATURE:
<221> NAME/KEY: variant
<222> LOCATION: (2)
<223> OTHER INFORMATION: Glu
<220> FEATURE:
<221> NAME/KEY: variant
<222> LOCATION: (3)
<223> OTHER INFORMATION: Val
<220> FEATURE:
<221> NAME/KEY: variant
<222> LOCATION: (4)
<223> OTHER INFORMATION: Gly
<220> FEATURE:
<221> NAME/KEY: variant
<222> LOCATION: (5)
<223> OTHER INFORMATION: Phe
<220> FEATURE:
<221> NAME/KEY: variant
<222> LOCATION: (6)
<223> OTHER INFORMATION: Pro
<220> FEATURE:
<221> NAME/KEY: variant
<222> LOCATION: (7)
<223> OTHER INFORMATION: 2497:<223 Val
<220> FEATURE:
<221> NAME/KEY: variant
<222> LOCATION: (8)
<223> OTHER INFORMATION: Arg
<220> FEATURE:
<221> NAME/KEY: variant
<222> LOCATION: (9)
<223> OTHER INFORMATION: Pro
<220> FEATURE:
<221> NAME/KEY: variant
<222> LOCATION: (10)
<223> OTHER INFORMATION: Gln
<220> FEATURE:
<221> NAME/KEY: variant
<222> LOCATION: (11)
<223> OTHER INFORMATION: Val
<220> FEATURE:
<221> NAME/KEY: variant
<222> LOCATION: (12)
<223> OTHER INFORMATION: Pro
<220> FEATURE:
<221> NAME/KEY: variant
<222> LOCATION: (13)
<223> OTHER INFORMATION: Leu
<220> FEATURE:
<221> NAME/KEY: variant
<222> LOCATION: (14)
<223> OTHER INFORMATION: Arg
<220> FEATURE:
<221> NAME/KEY: variant
<222> LOCATION: (15)
<223> OTHER INFORMATION: Pro
<220> FEATURE:
<221> NAME/KEY: variant
<222> LOCATION: (16)
<223> OTHER INFORMATION: Met
<220> FEATURE:
<221> NAME/KEY: variant
<222> LOCATION: (17)
<223> OTHER INFORMATION: Thr

```
-continued

<220> FEATURE:
<221> NAME/KEY: variant
<222> LOCATION: (18)
<223> OTHER INFORMATION: Tyr
<220> FEATURE:
<221> NAME/KEY: variant
<222> LOCATION: (19)
<223> OTHER INFORMATION: Lys
<220> FEATURE:
<221> NAME/KEY: variant
<222> LOCATION: (20)
<223> OTHER INFORMATION: Ala
<220> FEATURE:
<221> NAME/KEY: variant
<222> LOCATION: (21)
<223> OTHER INFORMATION: Ala
<220> FEATURE:
<223> OTHER INFORMATION: Description of Artificial Sequence: SYNTHETIC
      CONSTRUCT

<400> SEQUENCE: 18

Glu Glu Val Gly Phe Pro Val Arg Pro Gln Val Pro Leu Arg Pro Met Thr Tyr
  1               5                  10                 15

Lys Ala Ala
    20
```

HIV-1 PEPTIDE, ANTIGEN, IMMUNOGENIC COMPOSITION, DIAGNOSTIC METHOD AND IMMUNOASSAY KIT

This application is a national phase filing of PCTNO01/00363, filed Sep. 3, 2001.

The present invention relates to novel peptides based on conserved regions of the regulatory and auxiliary HIV proteins, antigens in free or carrier-bound form comprising at least one of the said peptides, vaccine compositions containing at least one of the antigens, immunoassay kits and a method of detecting antibodies, induced by human immunodeficiency virus (HIV) or HIV-specific peptides, using such antigens.

BACKGROUND

Human immunodeficiency virus type 1 (HIV-1), the causative agent of acquired immunodeficiency syndrome (AIDS) continues to present a formidable challenge to health in developing countries. In the Western world, therapeutic strategies that target HIV-1 replication and maturation have had a prominent impact on disease progression. The high cost of current treatment, high toxicity of the drugs and lack of cure, however, means that the development of safe and effective vaccines remains paramount for control of the AIDS pandemic.

HIV-1 is a complex retrovirus encoding six regulatory and auxiliary genes not found in the simple retroviruses, namely, tat, rev, nef, vif, vpr and vpu (Table 1). In eukaryotic cells, only completely spliced mRNAs are exported to the cytoplasm for translation. Unspliced or partially spliced RNAs are retained and eventually degraded in the nucleus. In this way, proteins encoded by the tat, rev and nef genes (designated Tat, Rev and Nef) derived from multiply spliced RNA species, are expressed first and constitute early HIV-1 gene expression. In order to express singly spliced RNAs and also to transport the full length unspliced RNA genome into the cytoplasm for packaging, HIV-1 has developed means to overcome the restrictions on RNA transport. The regulatory proteins, Tat and Rev, are essential for HIV-1 replication since mutations in these proteins eliminate HIV-1 production (Dayton A. I., et.al. (1986) Cell, 44:941–947, and Fisher, A. G., et.al. (1986) Nature, 320:367–371.).

The auxiliary genes are derived from exons positioned entirely upstream of the HIV-1 envelope gene e.g. vif or exons upstream of as well as within env but in different reading frames e.g. tat, rev. The efficiency of splicing in part regulates the levels of gene expression of the different auxiliary proteins.

Following integration of HIV-1 proviral DNA, predominantly truncated forms of mRNA are synthesised by the cellular RNA polymerase II which interacts with sites on the 5' long terminal repeat (LTR) of the proviral DNA. tat is one of the first genes to be expressed and carries a nuclear localisation signal. It is a potent transcriptional activator that enhances LTR-directed transcription up to a thousand fold. Continuous expression of Tat ensures a positive feed back loop for continued high level gene expression. Unlike conventional transcriptional activators that interact with DNA sequences, Tat binds directly to the 5' ends of all HIV-1 RNAs at a specific stem-loop secondary structure, TAR (transactivating response element). The structure of the loop is highly conserved and essential for Tat function. The structure of the Tat/TAR interaction has been analysed using nuclear magnetic resonance (NMR) (Puglisi et al. (1992) Science, 257:76–80). Tat binds TAR in association with the cellular protein, cyclin T, which in turn binds CDK9 that phosphorylates the RNA polymerase II C-terminal domain, thereby promoting the elongation of RNA transcripts. These Tat cellular cofactors are only present in activated cells, their absence represses transcription of proviral DNA resulting in a 'quasi latency' in T lymphocytes. Tat is expressed from two exons, both the nuclear localisation signal and the TAR binding region are located in the first exon. Tat is secreted from infected cells and can exert heterologous effects on neighbouring cells. These include cellular activation (Hofman et al. (1993) Blood, 82:2774–2780.), induction of cellular apoptosis (Macho et al. (1999) Oncogene, 18:7543–7551.1999) functioning as a secretable growth factor (Trinh, D. P. et.al. (1999) Biochem. Biophys. Res. Commun., 256:299–306.) and modulating host cell protein synthesis in favour of viral protein synthesis (Xiao et al. (1998) Biochem. Biophys. Res. Commun., 244:384–389.1998). Therapeutic strategies targeting Tat will therefore have a strong impact on HIV-1 infection.

The small multiply spliced mRNAs encoding Tat, Rev and Nef predominate during early phase after infection. When a threshold level of Rev is produced, unspliced and singly spliced RNAs accumulate in the cytoplasm for translation, allowing productive infection to proceed. Failure to generate this threshold level of Rev may contribute to HIV quasi latency. Rev can only bind to RNAs carrying an RNA structure, RRE (Rev responsive element) which is located in the env coding region of the genome. Rev interacts with the RRE as a multimer through a basic arginine rich region present in the amino terminal half of the protein. A consequence of this interaction is the transport of partially spliced RNAs that will provide gene products such as Env, Vif, Vpu and Vpr as well as unspliced RNAs that will serve as new genomes for incorporation into assembling particles. Structural analysis of the Rev/RRE interaction has also been carried out using NMR (Battiste et al. (1996) Science, 273:1547–1551.1996). Rev carries a leucine rich export signal that allows it to shuttle between the nucleus and the cytoplasm for continued transport of newly synthesised RNAs (Kalland et al. (1994). J. Virol., 68:1475–1485; Meyer & Malim, (1994) Genes Dev., 8:1538–1547.). In this way, Rev ensures that the structural genes are expressed late following the regulatory genes. Therapeutic strategies directed against Rev will interrupt the viral life cycle early in infection.

Although originally described as a negative factor, Nef has later been shown to have positive effects on virus replication and is expressed in larger quantities than that of Tat and Rev, both early and throughout infection. Nef is myristylated at the N-terminus and is associated with the inner side of the plasma membrane. Nef is partly responsible for down regulation and degradation of surface CD4 by endocytosis (Piguet et al. (1998) EMBO J., 17:2472–2481.). Removing CD4 from the cell surface prevents superinfection with other HIV-1 strains, or reinfection with newly released virus. Nef is also responsible for the down regulation of MHC class I thereby protecting infected cells from destruction by cytotoxic T-lymphocytes (Le Gall et al. (1997). Res. Virol., 148:43–47.). Nef is not an essential viral protein since it is not required for in vitro infection of peripheral blood lymphocytes or T-cell lines. Nef deletion mutants, however, are less pathogenic over long periods of time. Nef also has complex effects on signal transduction pathways in the cell and contains a proline rich region that can interact with the SH3 domain of kinases involved in T-cell activation, a feature necessary for efficient HIV replication (Moarefi et al. (1997). Nature, 385:650–653.). Nef containing viruses are capable of more viral DNA synthesis than viruses deleted in the Nef gene which suggests that Nef directly or indirectly activates the viral reverse transcriptase. The low level of Nef associated with virions may be responsible for this phenomenon. Low levels of Nef are also released from infected cells although the potential effect on neighbouring cells is unclear. Since Nef is expressed early in infection and has significant effects on CD4 and MHC class I expression as well as disease progression, it represents an important target for future therapeutic strategies.

Tat and Nef are secreted and can be taken up by macrophages and expressed in association with MHC class II molecules. This improves their suitability as targets for peptide based therapies which also would be expressed in the context of MHC class II. It is clear that targeting early gene products that are essential for HIV-1 replication, such as Tat and Rev should be given priority in addition to Nef which is also expressed early and influences disease progression.

Naturally occurring HIV sequences in vaccine candidates are not capable of stimulating a stable longterm immune response due to HIVs inherent ability to hide by changing the appearance of the epitopes presented for the immune system. To overcome this variable presentation of epitopes, certain amino acid substitutions and amino acid combinations will support the immune system to present and recognize these foreign virus antigens in a reliable manner and thus to a greater extent.

Based on the above background, we decided to investigate the possibility of designing novel synthetic peptides which can mimic the epitopes from the regulatory and auxiliary HIV proteins in such a way that they can be exposed for both the humoral as well as the cellular part of the immune system, to meet the need for an effective therapeutic and/or prophylactic vaccine.

The initital work was based on the native Tat amino acid sequences published by Korber B., et al., Human Retrovi-

TABLE 1

HIV-1 Regulatory and auxiliary proteins.

| Gene | Protein | Name | Expression | Localisation | Functions |
|---|---|---|---|---|---|
| Tat | Tat | Transactivator of viral transcription | Early | Nucleus | Activates viral transcription. Secreted from infected cells where it can activate T-cells, induce apoptosis and function as a growth factor. |
| Rev | Rev | Nuclear RNA export factor | Early | Nucleolus, nucleoplasm, cytoplasm | Regulates splicing/RNA transport to the cytoplasm. A shuttle protein. |
| Nef | Nef | Numerous effector functions | Early | Cytoplasm, membrane associated. Virions | Triggers CD4 endocytosis, Down regulates MHC class 1 expression. Binds to kinases and may influence T-cell signalling and activation. |
| Vpu | Vpu | Viral protein u | Late | Cytoplasm, membrane associated | Triggers intracellular CD4 degradation, down regulates MHC class 1, nonspecific promoter of retroviral particle release. |
| Vif | Vif | Viral infectivity factor | Late | Cytoplasm, membranes Virions | Enhances infectivity of viral particles in a cell dependent manner. Improves viral DNA synthesis during reverse transcription. |
| Vpr | Vpr | Viral protein r | Late | Predominantly nucleus Virions | Contributes to nuclear import of preintegration complex. Arrests cells in G2/M phase of the cell cycle. | ruses and AIDS 1997 Eds.Theoretical Biology and Biophysics Group, Los Alamos National Laboratory, Los Alamos, N. Mex. The first Tat epitope is located between amino acid 1 and amino acid 24 of the tat protein:

TABLE 2

Tat epitope

| AA no | Naturally occurring AAs | | | | | | |
|---|---|---|---|---|---|---|---|
| 1 | M | S | | | | | |
| 2 | E | D | V | | | | |
| 3 | S | Q | P | L | V | A | |
| 4 | V | I | | | | | |
| 5 | D | N | | | | | |
| 6 | P | H | A | | | | |
| 7 | R | N | S | K | E | D | |
| 8 | L | I | Q | R | V | M | T |
| 9 | E | D | P | | | | |
| 10 | P | S | | | | | |
| 11 | W | | | | | | |
| 12 | K | N | E | H | L | | |
| 13 | H | R | Q | | | | |
| 14 | P | | | | | | |
| 15 | G | P | | | | | |
| 16 | S | N | A | | | | |
| 17 | Q | K | T | | | | |
| 18 | P | H | | | | | |
| 19 | K | T | S | A | R | P | E | Q |
| 20 | T | A | I | | | | |
| 21 | A | P | D | V | | | |
| 22 | C | S | | | | | |
| 23 | T | N | S | | | | |
| 24 | N | K | R | Q | A | P | T |

The one letter as well as the three letter codes defining the amino acids in the sequences given throughout this specification are in accordance with International standards and given in textbooks, for instance Lehninger A. L., <<Principles of Biochemistry>>, Worth Publishers Inc., New York, 1982. The amino acids given to the right of the left column, represent the natural variation of the sequence. Our analyses resulted in a sequence containing this modified epitope:

C S W V N P R L E P W L H P G S Q P NI T A C T N
|_____|

Wherein NI indicates 2-aminohexanoic acid (Norleucine, abbreviated Nle and NI in the three letter and one letter code, respectively) and the cysteine residues are in an oxidized state, i.e. are forming an intrachain disulphide bridge. Since the Cystein residue to the C-terminal part (in position 22) of the peptide is part of an intramolecular disulfide bond outside this selected epitope, a similar intrapeptide disulphide bond is formed by placing a Cystein in the N-terminal part of the selected epitope. Another alternative is to form an intermolecular disulphide bond by dimerization of the sequences:

W V N P R L E P W L H P G S Q P NI T A C T N
                                           |
                                           |
W V N P R L E P W L H P G S Q P NI T A C T N

A further alternative is dimerization with another epitope selected from Tat. The second epitope on Tat is located between amino acid 35 and 57 in C-terminal direction, separated from the first epitope by 10 amino acids containing 5 Cys residues in addition to the Cys residue in each of the epitopes. The relatively high number of Cys residues offers a variety of inter- and intramolecular crosslinking possibilities. It is likely that this Cys-rich domain will dominate the immunological exposure of this protein and hence cause a "hiding" of the two relevant epitopes. Selection and modification of the two adjacent epitopes can expose an essential part of the Tat protein in a more optimal way.

In order to reduce the probability for development of escape mutants, the number of epitopes is further increased and two additional peptide sequences were selected. These sequences are located on Rev (residues 58–78) and Nef (residues 65–85). The native sequences have been published in Human Retroviruses and AIDS 1999; A Compilation and Analysis of Nucleic Acid and Amino Acid Sequences. Eds.Theoretical Biology and Biophysics Group, Los Alamos National Laboratory, Los Alamos:

TABLE 3

Tat epitope

| AA no. | Naturally occurring AAs | | | | | |
|---|---|---|---|---|---|---|
| 35 | Q | P | I | L | T | Y | V |
| 36 | V | A | C | L | | | |
| 37 | C | | | | | | |
| 38 | F | | | | | | |
| 39 | I | L | Q | M | T | | |
| 40 | T | N | K | R | | | |
| 41 | K | Q | | | | | |
| 42 | G | A | | | | | |
| 43 | L | | | | | | |
| 44 | G | S | | | | | |
| 45 | I | | | | | | |
| 46 | S | F | Y | | | | |
| 47 | Y | N | | | | | |
| 48 | G | | | | | | |
| 49 | R | K | S | | | | |
| 50 | K | | | | | | |
| 51 | K | | | | | | |
| 52 | R | | | | | | |
| 53 | R | K | S | G | | | |
| 54 | Q | R | P | | | | |
| 55 | R | | | | | | |
| 56 | R | | | | | | |
| 57 | R | G | S | | | | |

TABLE 4

Rev epitope:

| AA no. | Naturally occurring AAs | | | | | | |
|---|---|---|---|---|---|---|---|
| 58 | R | W | Q | | | | |
| 59 | I | V | L | F | | | |
| 60 | L | I | P | | | | |
| 61 | G | S | N | D | C | V | T | A | R |
| 62 | T | A | D | N | S | | |
| 63 | Y | C | F | R | H | S | V | L |
| 64 | L | V | | | | | |
| 65 | G | H | | | | | |
| 66 | R | G | | | | | |
| 67 | S | P | F | L | | | |
| 68 | A | T | E | Q | V | P | S |
| 69 | E | K | Q | D | N | | |
| 70 | P | S | A | N | | | |
| 71 | V | N | G | P | | | |
| 72 | P | Q | H | S | L | R | T | D | I |
| 73 | L | F | V | | | | |
| 74 | Q | L | P | H | D | E | |
| 75 | L | | | | | | |
| 76 | P | | | | | | |
| 77 | P | L | E | | | | |
| 78 | L | I | V | P | | | | and the

TABLE 5

Nef epitope, Table 5:

| AA no. | Naturally occurring AAs | | | |
|---|---|---|---|---|
| 65 | E | G | D | S |
| 66 | N | G | D | E |
| 67 | E | V | | |
| 68 | A | G | | |
| 69 | L | F | | |
| 70 | P | | | |
| 71 | I | V | | |
| 72 | T | R | K | A | M |
| 73 | P | | | |
| 74 | Q | H | | |
| 75 | V | L | I | |
| 76 | P | | | |
| 77 | L | V | T | |
| 78 | R | | | |
| 79 | P | | | |
| 80 | M | V | I | |
| 81 | T | D | | |
| 82 | Y | F | R | |
| 83 | K | R | | |
| 84 | A | G | S | E | Q |
| 85 | A | S | V | |

Several modified peptides have been synthesized in order to determine the uniqueness of the sequences as well as their properties for stimulation of the immune system in combination with their specificity and sensitivity as HIV-1 antigens.

DESCRIPTION OF THE INVENTION

The peptides according to the invention are originating from the four different conserved areas of the HIV-1 Tat, Rev and Nef proteins which are described above, having the properties of maintaining the uniqueness (immunogenicity, sensitivity and specificity) of the HIV-1 epitopes. Further the new peptides according to the invention possess no recognized cytotoxic T lymphocyte (CTL) antagonistic effect and shall have at least one potential CTL epitope.

The peptides, according to the invention, which have met the above criteria are from the following groups;

$Xaa_1$ $Xaa_2$ $Xaa_3$ $Xaa_4$ $Xaa_5$ $Xaa_6$ $Xaa_7$ Leu     (SEQ ID NO: 1)

Glu Pro Trp $Xaa_{12}$ His Pro $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ wherein the amino acids of the chain could have the following meanings;
   Xaa in position 1 of the peptide derivative is Met, Ser, Cys or none,
   Xaa in position 2 is Glu, Asp, Val, Ser or none
   Xaa in position 3 is Ser, Gln, Pro, Leu, Val, Ala, Trp, Tyr or Phe,
   Xaa in position 4 is Val or Ile,
   Xaa in position 5 is Asp, Asn or Ile,
   Xaa in position 6 is Pro, His or Ala,
   Xaa in position 7 is Arg, Asn, Ser, Lys, Glu or Asp
   Xaa in position 12 is Leu, Ile or Nle
   Xaa in position 15 is Gly or Pro
   Xaa in position 16 is Ser, Asn or Ala,
   Xaa in position 17 is Gln, Lys or Thr
   Xaa in position 18 is Pro or His,
   Xaa in Position 19 is Lys, Thr, Ser, Ala, Arg, Pro, Glu, Leu, Ile or Nle
   Xaa in position 20 is Thr, Ala or Ile
   Xaa in position 21 is Ala, Pro, Asp or Val
   Xaa in position 22 is Cys or Ser
   Xaa in position 23 is Thr, Asn or Ser
   Xaa in position 24 is Asn, Lys, Arg, Gln, Ala Pro or Thr the peptide comprises at least six consecutive amino acids of the sequence of SEQ ID NO: 1,
   furthermore two or more of the Cys residues may form part of an intrachain- or interchain disulphide binding, a $-S-(CH_2)_p-S-$ or a $-(CH_2)_p$-bridge wherein p=1–8, optionally intervened by one or more hetero atoms such as O, N or S, $Xaa_1$ $Xaa_2$ $Xaa_3$ Phe $Xaa_5$ $Xaa_6$ $Xaa_7$     (SEQ ID NO: 4)

$Xaa_8$ $Xaa_9$ $Xaa_{10}$ $Xaa_{11}$ $Xaa_{12}$ -Z- Tyr $Xaa_i$ Gly $Xaa_{15}$ Lys Lys Arg $Xaa_{19}$ $Xaa_{20}$ $Xaa_{21}$ $Xaa_{22}$ $Xaa_{23}$ wherein the amino acids of the chain have the following meaning;
   Xaa in position 1 is Pro, Ile, Leu, Thr, Tyr or Val
   Xaa in position 2 is Val, Ala Cys, Leu,
   Xaa in position 3 is Cys, Ile, Leu, Val or Nle
   Xaa in position 5 is Ile, Leu, Gln, Met or Thr
   Xaa in position 6 is Thr, Asn, Lys or Ara
   Xaa in position 7 is Lys, Arg or Gln
   Xaa in position 8 is Gly or Ala
   Xaa in position 9 is Leu or Ile
   Xaa in position 10 is Gly, Ser or Ala
   Xaa in position 11 is Ile or Gly
   Xaa in position 12 is Ser, Phe or Tyr
   $Xaa_i$ inserted before position 14 is Leu, Ile, Nle
   Xaa in position 15 is Arg, Lys, Ser or Citrulline (Cit)
   Xaa in position 19 is Arg, Lys, Ser, Gly or Cit
   Xaa in position 20 is Gln, Arg or Pro
   Xaa in position 21 is Ile or leu
   Xaa in position 22 is Gly, Leu, Ile, Cys or none
   Xaa in position 23 is Gly or none wherein the sequence of SEQ ID NO: 4 comprises at least six consecutive amino acids, -Z- is an optional linker and have the meaning PEG, modified PEG and/or $[Gly]_n$ wherein n=1, 2 or 3,
   furthermore two or more of the Cys residues may form part of an intrachain- or interchain disulphide binding, a $-S-(CH_2)_p-S-$ or a $-(CH_2)_p$-bridge wherein p=1–8, optionally intervened by one or more heteroatoms such as O, N or S, $Xaa_1$ Ile Leu $Xaa_4$ $Xaa_5$ $Xaa_6$ Leu Gly     (SEQ ID NO: 7)

Arg $Xaa_{10}$ $Xaa_{11}$ -Z- $Xaa_{12}$ Leu $Xaa_i$ $Xaa_i$ $Xaa_{14}$ $Xaa_{15}$ $Xaa_{16}$ $Xaa_{17}$ $Xaa_{18}$ $Xaa_{19}$ Leu Pro Pro Leu wherein Xaa in position 1 is Phe, Tyr, Trp or Arg
   Xaa in position 4 is Gly, Ser, Asn, Asp, Cys, Val, Thr, Ala, or Arg
   Xaa in position 5 is Thr, Ala, Asp, Asn or Ser Xaa in position 6 is Tyr, Cys, Phe, Arg, His, Ser, Val or Leu Xaa in position 10 is Ser, Pro, Phe, Leu or Ile Xaa in position 11 is Ala, Thr, Glu, Gln, Val Pro or Ser Xaa in position 12 is Glu, Lys, Gln, Asp, Asn, Tyr, Trp or Phe Xaa$_i$ inserted after position 13 is Ser, Pro, Phe, Leu or Ile Xaa$_i$ inserted before position 14 is Ala, Thr, Glu, Gln, Val, Pro, or Ser Xaa in position 14 is Glu, Lys, Gln, Asp or Asn Xaa in position 15 is Pro, Ser, Ala or Asn Xaa in position 16 is Val, Asn, Gly or Pro Xaa in position 17 is Pro, Gln, His, Ser, Leu, Arg, Thr, Asp or Ile Xaa in position 18 is Leu Phe or Val Xaa in position 19 is Gln, Leu, Pro, His, Asp or Glu wherein the sequence of SEQ ID NO: 7 consists of at least six consecutive amino acids, the linker -Z- is optional and have the meaning PEG, modified PEG and/or [Gly]$_n$ wherein n=1, 2 or 3, Xaa$_1$ Leu Val Gly Xaa$_5$ Pro Xaa$_7$    (SEQ ID NO: 10)

Xaa$_8$ Pro Xaa$_{10}$ Xaa$_{11}$ Pro -Z-[Arg]$_m$

Xaa; Xaa$_{13}$ Xaa$_{14}$ Pro Xaa$_{16}$ Xaa$_{17}$

Xaa$_{18}$ Xaa$_{19}$ Xaa$_{20}$ Xaa$_{21}$ wherein the Xaa in position 1 is Lys or Arg Xaa in position 5 is Phe or Leu Xaa in position 7 is Ile or Val Xaa in position 8 is Thr, Arg, Lys, Ala or Met Xaa in position 10 is Gln or His Xaa in position 11 is Val, Leu or Ile Xaa$_i$ inserted before position 13 is Leu Xaa in position 13 is Leu, Val or Thr Xaa in position 14 is Arg or Citrulline (Cit)

Xaa in position 16 is Met, Val, Ile or Nle, Leu

Xaa in position 17 is Thr or Asp

Xaa in position 18 is Tyr, Phe or Arg

Xaa in position 19 is Lys or Arg

Xaa in position 20 is Ala, Gly, Ser, Glu or Gln

Xaa in position 21 is Ala, Ser or Val wherein the sequence of SEQ ID NO: 10 consists of at least six consecutive amino acids, the linker -Z- is optional and have the meaning PEG, modified PEG and/or [Gly]$_n$ wherein n=1, 2 or 3 and independently from n, m in [Arg]$_m$ is=0, 1, 2 or 3, the terminal ends of the sequences may be free carboxyl- or amino groups, amides, acyls, acetyls or salts thereof, and/or the said peptide sequences are immobilized to a solid support.

The new peptide sequences have the potential to serve as a good antigen wherein the antigen comprises at least one peptide selected from the group of sequences of SEQ ID NO: 1, SEQ ID NO: 4, SEQ ID NO: 7 or SEQ ID NO: 10. The antigenicity may be adapted through adjusting the ratio or concentration of different peptides or size of the peptides by for instance dimerization or polymerization and/or immobilization to a solid phase. The antigen comprises one or more polypeptide sequences, according to the invention, which could be either linked by a bridge for instance a disulphide bridge between the Cys residues of the chains or bridges like $C_1$–$C_8$ alkylen possibly intervened by one or more heteroatoms like O, S, or N or preferably they are unlinked. The chains may be immobilized to a solid phase in monomeric, dimeric or oligomeric forms. Further amino acids may be added to the ends in order to achieve an "arm" to facilitate immobilization.

PEG is polyethylene glycol (HO(CH$_2$CH$_2$O)$_a$H and can be part of the linker -Z-, optionally PEG is modified by a dicarboxylic acid (HO(CH$_2$CH$_2$O)$_a$CO(CH$_2$)$_b$COOH) or a terminal carboxylic group (HO(CH$_2$CH$_2$O)$_{a-1}$CH$_2$COOH) where a=1–10 and b=2–6, prior to linking.

The linker -Z- can either consist of PEG, modified PEG, or a combination thereof and/or one or more Gly residues combined. Alternatively the linker -Z- can consist of a Gly-bridge [Gly]$_n$ where n=1, 2 or 3.

All amino acids in the peptides of the invention can be in both D- or L-form, although the naturally occurring L-form is preferred.

The C- and N-terminal ends of the peptide sequences could deviate from the natural sequences by modification of the terminal NH$_2$-group and/or COOH-group, they may for instance be acylated, acetylated, amidated or modified to provide a binding site for a carrier or another molecule.

The peptides according to the invention are consisting of 6 to 50 amino acids, preferably between 10 and 30 amino acids. They are covering all natural variation of amino acids in the identified positions.

The polypeptide antigen according to the invention is either in a free or in a carrier-bound form. The carrier or solid phase to which the peptide is optionally bound can be selected from a vide variety of known carriers. It should be selected with regard to the intended use of the immobilized polypeptide as a diagnostic antigen or as an immunizing component in a vaccine.

Examples of carriers that can be used for e.g. diagnostic purposes are magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatine or polysaccharide particles or other protein particles, red blood cells, mono- or polyclonal antibodies or fab fragments of such antibodies.

According to a further embodiment of the present invention, the antigens may form part of a vaccine possibly combined with carriers, adjuvants or combined with other immunostimulating elements such as canarypox virus carrying the env gene. Examples of carriers and/or adjuvants for vaccine purposes are other proteins such as human or bovine serum albumin and keyhole limpet haemocyanin and fatty acids. Immunostimulatory materials may be divided into three groups; adjuvants, carriers for antigens and vehicles. Examples of adjuvants include aluminum hydroxyd, aluminum salts, saponin, muramyl di and tripeptides, monophosphoryl lipid A, palmitic acid, B.pertussis and various cytokines including the Th1 cytokine IL-12 and IL-1. A number of protein toxins can be used to carry passenger proteins across cellular membranes into the cytosol, which are useful in developing CTL vaccines. Carriers include bacterial toxoids such as inactivated tetanus and cholera toxins, genetically detoxified bacterial toxins such as heat labile enterotoxin from E.coli, fatty acids, live vectors such as polio chimeras and hybrid proteins that form particulates for example yeast retrotransposon hybrid TY particles and HBcAg particles. Vehicles which are frequently occurring components in modern vaccines are consisting of mineral oil emulsion, Freunds complete and incomplete adjuvant, vegetable oil emulsions, nonionic block co-polymer surfactants, squalene or squalane, lipopeptides, liposomes and biodegradable microspheres. Two novel adjuvants which possess significant potential for the development of new vaccines include an oil-in-water microemulsion (MF59) and polymeric microparticles. Any substance that can enhance the immunogenicity of the antigen may be used and several further alternatives of carriers or adjuvants are given in the US or European Pharmacopoeia.

A suitable formulation of the antigen for immunostimulatory uses may also comprise interferons such as INF-γ, antiviral chemokines or haematopoietic growth factors such as granulocyte macrophage growth factor.

Another approach in order to enhance the stimulation and absorption in for instance the intestine is to administer the peptides of the invention, with small peptides such as di, tri or tetrapeptides. These peptides can be administered in addition to or in combination with the peptides of the invention. Preferably the peptides are administered together with the tripeptide YGG, consisting of amino acids in the D- or L-forms, preferably in the D-form.

Recent approaches to non-parenteral delivery of vaccines, for instance via mucosa include; gene fusion technology to create non-toxic derivatives of mucosal adjuvants, genetically inactivated antigens with a deletion in an essential gene, coexpression of an antigen and a specific cytokine that is important in the modulation and control of a mucosal immune response, and genetic material itself that would allow DNA or RNA uptake and its endogenous expression in the host's cells.

One approach for developing durable responses where cell-mediated immunity is required, is to vaccinate with plasmid DNA encoding one or more specific antigen(s).

In order to protect against HIV infection, vaccines should induce both mucosal and systemic immune responses and could be administered by any convenient route, parenterally or non-parenterally, such as subcutanously, intracutanously, intravenously, intramuscularly, perorally, mucosally or intranasally for example.

In a preferred embodiment of the vaccine according to the present invention it comprises antigens containing peptides selected from at least one of the groups of the SEQ ID NO: 1, 4, 7 and 10, more preferred the different peptides occur in equal amounts.

In a further preferred embodiment the vaccine composition contains the antigens;

F V I H R L E P W L H P G S Q H NI (SEQ ID NO: 14)

T A S T N - $NH_2$ and

R L V G F P V K P Q V P G L L R P  (SEQ ID NO: 15)

L T Y K A A - $NH_2$.

The sequences can activate the cellular immune system, and contribute with CTL-epitopes. The amino acid changes implemented within the frame of the CTL-epitopes are designed to achieve enhanced binding. Other amino acid changes have been conducted in order to facilitate the synthesis of the peptide and/or increase the solubility of the peptide.

A method for detecting antibodies, induced by HIV-1 or HIV-1 specific peptides or proteins, in a sample of body fluid using the present antigens is a further embodiment of the invention. Also immunoassay kit designed for this detection and antibodies capable of selectively reacting with the said antigens are encompassed by the present invention.

Description of the Preparation of the Peptides

The peptides of the invention can be produced by any known method of producing a linear amino acid sequence, such as recombinant DNA techniques. A nucleic acid sequence that encodes one or more peptides of the invention or a multimer of the said peptides, is introduced into an expression vector. Suitable expression vectors are for instance plasmids, cosmids, viruses and YAC (yeast artifical chromosome) which comprise necessary control regions for replication and expression. The expression vector may be stimulated to expression in a host cell. Suitable host cells are for example bacteria, yeast cells and mammal cells. Such techniques are well known in the art and described for instance by Sambrook et al., Molecular Cloning: A Laboratory Manual, Cold Spring Harbor Laboratory Press, Cold Spring Harbor, 1989. Other well-known techniques are degradation or synthesis by coupling of one amino acid residue to the next one in liquid phase or preferably on a solid phase (resin) for instance by the so-called Merrifield synthesis. See for instance Barany and Merrifield in the Peptides, Analysis, Synthesis, Biology, Vol. 2, E. Gross and Meinhofer, Ed. (Acad.Press, N.Y., 1980), Kneib-Coronier and Mullen Int. J. Peptide Protein Res., 30, p. 705–739 (1987) and Fields and Noble Int. J. Peptide Protein Res., 35, p. 161–214 (1990).

In case a linked or cyclic peptide is desired, the amino acid sequence is subjected to a chemical oxidation step in order to cyclize or link the two cysteine residues within one or between two peptide sequences, when the appropriate linear amino acid sequences are synthesized, see Akaji et al., Tetrahedron Letter, 33, 8, p. 1073–1076, 1992.

General Description of Synthesis

All peptide derivatives prepared in the Examples given below were synthesized on a Milligen 9050 Peptide Synthesizer using a standard program. The resin used was Tenta Gel P RAM with a theoretical loading of 0.20 meq/g (RAPP POLYMERE GmbH, Tübingen). The final product of the synthesis was dried in vacuuo overnight. The peptide was then cleaved from the resin by treatment with 90% trifluoroacetic acid in the presence of ethandithiol (5%) and water (5%) as scavengers (1.5 hours at RT). Then the resin was filtered and washed on filter with additional trifluoro acetic acid (100%) (2×20 ml). The combined filtrates were evaporated in vacuuo (water bath at RT) and the residue was triturated with ethyl ether (200 ml) and the precipitated product filtered off. The solid was promptly dissolved on filter with glacial acetic acid (100 ml) and added to 1.5 l of 20% acetic acid in methanol and treated with 0.1 M solution of iodine in methanol until a faint brown colour remained. Then Dowex 1×8 ion exchange in acetate form (15 g) (Bio-Rad, Richmond, Calif.) was added and the mixture filtered. The filtrate was evaporated and the residue freeze-dried from acetic acid. The product was then purified by reversed phase liquid chromatography on a column filled with Kromasil® 100-5 C8 (EKA Nobel, Surte, Sweden) in a suitable system containing acetonitrile in 0.1% trifluoro acetic acid water solution. The samples collected from the column were analyzed by analytical high performance liquid chromatography (HPLC) (Beckman System Gold, U.S.A.) equipped with a Kromasil® 100-5 C8 Column (EKA Nobel, Surte, Sweden). Fractions containing pure substance were pooled, the solvent was evaporated and the product freeze-dried from acetic acid. The final HPLC analysis was per-formed on final product, and the structure of the peptide was confirmed by amino acid analysis and mass spectrometry (LDI-MS).

All amino acids used during the synthesis were L-amino acids and they were protected with a fluorenyl methoxy-carbonyl group at the α-amino function. The side chains were protected as follows:

Cys (Trt), Gln(Trt), Glu(OtBu), Thr(tBu).

The abbreviations, within the brackets are:

Trt=triphenyl methyl t-Bu=tert. Butyl

OtBu=tert. Butyl ester

The amino acid derivatives were supplied by Bachem AG, Switzerland.

EXAMPLE 1

Preparation of C S W V N P R L E P W NI H P G S Q H NI T A C T N —$NH_2$ (SEQ ID NO: 2). The peptide was synthesized in amide form, from the corresponding starting materials according to the general description of synthesis. The peptide was then cyclizated by oxidation with $I_2$. The peptide was dissolved in acetic acid/methanol (1:4) and 0.1 M $I_2$ in methanol was added. The purity was determined by HPLC analysis and the structure was confirmed by amino acid analysis and mass spectrometry (LDI-MS).

Purity (HPLC): more than 97% (single impurity less than 1%) Molecular weight (free base): 2746.2

EXAMPLE 2

Preparation of F V I P R L E P W NI H P G S Q P NI T A C T N —$NH_2$ (SEQ ID NO: 3). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 97% (single impurity less than 1%) Molecular weight (free base): 2538.0

EXAMPLE 3

Preparation of Y L L F L T K G L G I S G G G Y NI G Cit K K R Cit Q I L G —$NH_2$ (SEQ ID NO: 5). The peptide is synthesized in amide form, from the corresponding starting materials according to the general description of synthesis. The purity is determined by HPLC analysis and the structure is confirmed by amino acid analysis and mass spectrometry (LDI-MS).

EXAMPLE 4

Preparation of Y L NI F L T R G L G I S G G G Y NI G Cit K K R Cit Q I C G —$NH_2$ (SEQ ID NO: 6). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 97% (single impurity less than 1%) Molecular weight (free base): 3097.7

EXAMPLE 5

Preparation of R I L S T Y L G R I S G G G W L S A E P V P L Q L P P L —$NH_2$ (SEQ ID NO: 8). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 97% (single impurity less than 1%) Molecular weight (free base): 2990.6

EXAMPLE 6

Preparation of R I L S T Y L G R I S G G G Y L S A E P V P L Q L P P L —$NH_2$ (SEQ ID NO: 9). The peptide is synthesized in amide form, from the corresponding starting materials according to the general description of synthesis. The purity is determined by HPLC analysis and the structure is confirmed by amino acid analysis and mass spectrometry (LDI-MS).

EXAMPLE 7

Preparation of K L V G F P V K P Q V P G G G R L L Cit P NI T Y K A A —$NH_2$ (SEQ ID NO: 11). The peptide is synthesized in amide form, from the corresponding starting materials according to the general description of synthesis. The purity is determined by HPLC analysis and the structure is confirmed by amino acid analysis and mass spectrometry (LDI-MS).

EXAMPLE 8

Preparation of R L V G F P V K P Q V P G G G R L L R P L T Y K A A —$NH_2$ (SEQ ID NO: 12). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 97% (single impurity less than 1%) Molecular weight (free base): 2790.4 Molecular formula: $C_{130}H_{217}O_{39}N_{29}$

EXAMPLE 9

Dimerisation Via Disulphide Bridge.

The peptide sequences of the Example 2 are linked via an oxidation step to form a dipeptide wherein the cysteine residues form a disulphide bridge. The bridge is formed in either ways;

A) Oxidation with $I_2$. The peptides (equal amounts if different) are dissolved in acetic acid/methanol (1:4) and 0.1 M $I_2$ in methanol is added yielding a mixture of the homodimer, or B) Oxidation via [Cys(Spy)$^{22}$]-SEQ ID NO: 3. 2.3 mM of the peptide of SEQ ID NO: 3 dissolved in 2 M AcOH (aq) and 2-propanol (1:1) is treated with 2,2 dithio-dipyridin (3 eqv) to yield [Cys(Spy)$^{22}$]-SEQ ID NO: 3. [Cys(Spy)$^{22}$]-SEQ ID NO: 3 is dissolved in 10 mM $NH_4$Oac (aq pH=6, 5) and methanol (5:2) to yield the dimer of SEQ ID NO: 13.

The purity of the resulting dimer is determined by HPLC analysis and the structure is confirmed by amino acid analysis and mass spectrometry (LDI-MS).

EXAMPLE 10

Preparation of F V I H R L E P W L H P G S Q H NI T A S T N —NH$_2$(SEQ ID NO:14). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 98% (single impurity less than 1%) Molecular weight (free base): 2540.2

EXAMPLE 11

Preparation of R L V G F P V K P Q V P G L L R P L T Y K A A —NH$_2$ (SEQ ID NO:15). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 99% (single impurity less than 1%) Molecular weight (free base): 2520.3

EXAMPLE 12—REFERENCE EXAMPLE

Preparation of a nativ tat1 sequence; M E S V D P R L E P W K H P G S Q P K T A C T N —NH$_2$ (SEQ ID NO:16). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 97% (single impurity less than 1%) Molecular weight (free base): 2708.1

EXAMPLE 13—REFERENCE EXAMPLE

Preparation of a nativ tat2 sequence; Q V C F I T K G L G I S Y G R K K R R Q R R R—NH$_2$ (SEQ ID NO:17). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 94% Molecular weight (free base): 2806.4

EXAMPLE 14—REFERENCE EXAMPLE

Preparation of a nativ Nef sequence; E E V G F P V R P Q V P L R P M T Y K A A —NH$_2$ (SEQ ID NO:18). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 95% Molecular weight (free base): 2384.8

EXAMPLE 15

A vaccine comprising the peptides of the SEQ ID NO: 3 and 12 is prepared. The freeze-dried peptides are dissolved in sterile water at a final concentration of 4 mg/ml. A preparation of a granulocyte-macrophage-colony stimulating factor (GM-CSF) is also prepared, according to the manufacturers directions for use, to a final concentration of 0.3 mg/ml. The two solutions are administered intracutaneously. A typical injection dose is 100 µl.

EXAMPLE 16

A vaccine comprising the peptides of the SEQ ID NOS: 14 and 15 is prepared. The freeze dried peptides are dissolved in sterile water at a final concentration of 4 mg/ml. A preparation of a granulocyte-macrophage-colony stimulating factor (GM-CSF) is also prepared, according to the manufacturers directions for use, to a final concentration of 0.3 mg/ml. The two solutions are administered intracutaneously. A typical injection dose is 100 µl.

EXAMPLE 17

An antigen solution or suspension is mixed with equal parts of Freund's adjuvant of Behring, complete or incomplete, and is then finely emulsified by being drawn up into, and vigorously pressed out of, an injection syringe, or with a homogenator. The emulsion should remain stable for at least 30 minutes. The antigen-adjuvant emulsions is best injected subcutaneously as a depot.

EXAMPLE 18

Immunoassay for Detection of Antibodies Induced by HIV-1.

The magnetic particle reagents are to be prepared according to the manufacturers recommended protocol. Dynal AS, is the manufacturer of the Dynabeads, which are employed. The magnetic particles coated with ligand are called Reagent 1. A peptide according to the invention is covalently coupled to the pre-activated surface of the magnetic particles. It is also possible to physically absorb the peptide to the surface of the magnetic particles. The concentration of particles in Reagent 1 is within the range from 1 mg/ml to 15 mg/ml. The particle size varies between 0.2 µm to 15 µm. The concentration of peptides is within the range from 0.01 mg/mg particle to 1 mg/mg particle.

The anti human Ig Alkaline Phosphatase (AP) conjugated antibody reagent is prepared according to the recommended protocol of Dako AS. This protocol is a standard procedure in this field. This reagent is called Reagent 2.

The substrate solution phenolphtaleine-monophosphate is to be prepared according to the recommended protocol of Fluka AG. This protocol is a standard procedure in this field. The substrate solution is called Reagent 3.

The washing and incubation buffer which is used is standard 0,05M tris-base buffer with the following additional compounds; Tween 20 (0.01% to 0.1%), glycerol (0.1% to 10%) and sodium chloride (0.2% to 0.1%).

The assay procedure comprises an incubation step wherein 1 drop of Reagent 1 is mixed with 2 drops of washing buffer in each well. After mixing, 30 µl of sample is added and the solution is incubated for 5 minutes. The magnetic particles can be trapped by a magnet and the liquid removed, before the magnet is separated. Then the wells are washed twice in 4 drops of washing solution, before incubation with Reagent 2. 1 drop of Reagent 2 is added with 2 drops of washing buffer and the solution is incubated for 5 minutes. The magnetic particles can be trapped by a magnet and the liquid removed, before the magnet is separated. Then the washing step is repeated before incubation with Reagent 3. 2 drops of Reagent 3 is added to each well and the solution is incubated for 3 minutes. The results can be read against a white background. Positive results are red (3+=strong red) whereas negative results are clearly light yellow/brown solutions as obtained in the negative control.

The immunoassay kit could be used in detection of antibodies, induced either by HIV virus or HIV-specific peptides or proteins, for instance the peptides of the present invention.

EXAMPLE 19

Therapeutic or Prophylactic Vaccine.

At least one of the polypeptides of the invention, selected from the group of sequences SEQ ID NO: 1, SEQ ID NO: 4, SEQ ID NO: 7 or SEQ ID NO: 10 can form antigens and constitute the active principle of a prophylactic or therapeutic vaccine intended to provide protection against the human immunodeficiency virus type 1 (HIV-1). The vaccine may include compounds having beneficial effects in protecting or stimulating the hosts immune system (human being or vertebrate animal) for instance interleukins, interferons, granulocyte macrophage growth factors, haematopoietic growth factors or similar. Preferably the vaccine composition further contain an adjuvant or vehicle, more preferably the adjuvant or vehicle is Monophosphoryl Lipid A (MPL®) possibly with alum, Freund's adjuvant (complete or incomplete) or aluminum hydroxyd. The optimal amount of adjuvant/vehicle will depend on the type(s) which is chosen.

The peptides of the invention might be modified by C-terminal addition of a single fatty acid such as a single paimitoyl chain to form a lipopeptide vaccine. Further the lipopeptides can be introduced into liposome membranes by the freeze-thaw method resulting in liposomes bearing the peptide ligands on their surface.

The peptide or vaccine formulation can be freeze-dried prior to storage. The freeze-dried peptides can be dissolved in sterile water to a final concentration of 0.1–100 mg/ml. The vaccine may be stored preferably at low temperature, in ampoules containing one or more dosage units, ready for use. A typical dosage unit of the peptide according to the invention is within the concentration range: 0.05 µg–1 mg per kg bodyweight, preferably within 0, 15 µg–0.15 mg per kg body weight. Persons skilled in the art will appreciate that a suitable dose will depend on the body weight of the pasient, the type of disease, severity of condition, administration route and several other factors. When used as a therapeutic vaccine, the vaccine might be administered up to 12 times, through injections. Further boosters might follow and can in some cases take place throughout the patients life. In preparation of an injection solution the peptides are dissolved in sterile water at a final concentration of 1 mg/ml per peptide. Typically an injection volume is 100 µl to 200 µl (2×100 µl). The peptide is preferably co-administered with a suitable adjuvant and/or a granulocyte-macrophage growth factor for instance Leucomax® <<Shering Plough>> made within a concentration range of from 0.1 mg/ml to 1 mg/ml, or according to the manufacturers recommendations for use. Particularly preferred is a combination therapy where the present peptides are administered together with the peptides as described in the published International patent application no. PCT/NO00/00075 and/or the co-pending Norwegian patent application no. 2000 4413. These peptides may be administered simultaneously or sequentially. Suitable administration may be intracutane, subcutane, intravenous, peroral, intramuscular, intranasal, mucosal or any other suitable route. Booster administrations may be required in order to maintain protection. For persons skilled in the art it will be understood that the vaccine compositions according to the invention are useful not only in prevention of infection, but also in treatment of infection.

No toxic effects of the peptides according to the invention, are observed when injected in mice in a dosage of 100 µg per kg body weight.

The above Examples are only meant as illustrating the invention. It must be understood that a person skilled in the art can modify the peptides, antigens and vaccines herein described without deviating from the concept and scope of this invention as set forth in the claims.

The invention claimed is:

1. A composition comprising an isolated HIV peptide comprising an amino acid sequence of Phe Val Ile His Arg Leu Glu Pro Trp Leu His Pro Gly Ser Gln His Nle Thr Ala Ser Thr Asn (SEQ ID NO: 14),
wherein the terminal ends of the sequence may be free carboxyl- or amino groups, amides, acyls, acetyls or salts thereof, and
two or more of the Cys residues may form part of an intrachain- or interchain-disulfide bond, a —S—(CH$_2$)$_p$—S— or a —(CH$_2$)$_p$-bridge wherein p=1–8 optionally intervened by one or more heteroatoms such as O, N and S and/or the peptide is immobilized to a solid support.

2. An antigen comprising the peptide according to claim 1.

3. An immunogenic composition comprising the antigen according to claim 2 with a pharmaceutically acceptable diluent and optionally an adjuvant, carrier and/or vehicle and optionally additional immunostimulatory compound(s).

4. The immunogenic composition according to claim 3, wherein the peptide is dissolved in a sterile water solution and the optional immunostimulatory compound is a granulocyte macrophage colony stimulating factor.

5. The immunogenic composition according to claim 3, wherein the composition comprises an adjuvant selected from the group consisting of Monophosphoryl Lipid A (MPL®), Freund's complete adjuvant, Freund's incomplete adjuvant and aluminum hydroxide.

6. The immunogenic composition according to 3, wherein the antigen is formulated as a lipopeptide and/or a liposome formulation.

7. A method of detecting antibodies, induced by a HIV or HIV-specific peptide(s) or protein(s), in a sample of body fluid, comprising;
contacting the sample with the peptide according to claim 1 under conditions such that antigen-antibody binding occurs; and
detecting bound antibodies.

8. An immunoassay kit for the detection of antibodies, induced by a HIV or HIV-specific peptides or proteins, in a sample of body fluid, comprising the peptide according to claim 1.

9. The composition according to claim 1, further comprising an isolated HIV peptide selected from the group consisting of:
(1) Cys Ser Trp Val Asn Pro Arg Leu Glu Pro Trp Nle His Pro Gly Ser Gln His Nle Thr Ala Cys Thr Asn (SEQ ID NO: 2); and
(2) Phe Val Ile Pro Arg Leu Glu Pro Trp Nle His Pro Gly Ser Gln Pro Nle Thr Ala Cys Thr Asn (SEQ ID NO: 3),
wherein the terminal ends of the sequence may be free carboxyl- or amino groups, amides, acyls, acetyls or salts thereof, and
two or more of the Cys residues may form part of an intrachain- or interchain-disulfide bond, a —S—(CH$_2$)$_p$—S— or a —(CH$_2$)$_p$-bridge wherein p=1–8 optionally intervened by one or more heteroatoms such as O, N and S and/or the peptide is immobilized to a solid support.

* * * * *